(12) United States Patent
Mayse et al.

(10) Patent No.: US 9,283,053 B2
(45) Date of Patent: Mar. 15, 2016

(54) APPARATUS AND METHODS FOR IMPLANTING OBJECTS, SUCH AS BRONCHOSCOPICALLY IMPLANTING MARKERS IN THE LUNG OF PATIENTS

(75) Inventors: Martin L. Mayse, St. Louis, MO (US); Steven C. Dimmer, Bellevue, WA (US); Roger Hildwein, Fall City, WA (US); Eric D. Nielson, Bellevue, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1112 days.

(21) Appl. No.: 12/067,321

(22) PCT Filed: Sep. 19, 2006

(86) PCT No.: PCT/US2006/036585
§ 371 (c)(1),
(2), (4) Date: Sep. 25, 2009

(87) PCT Pub. No.: WO2007/035798
PCT Pub. Date: Mar. 29, 2007

(65) Prior Publication Data
US 2010/0036241 A1    Feb. 11, 2010

Related U.S. Application Data

(60) Provisional application No. 60/718,460, filed on Sep. 19, 2005, provisional application No. 60/833,931, filed on Jul. 28, 2006.

(51) Int. Cl.
*A61B 6/12* (2006.01)
*A61M 25/00* (2006.01)
(Continued)

(52) U.S. Cl.
CPC ............. *A61B 19/54* (2013.01); *A61B 19/5244* (2013.01); *A61B 1/2676* (2013.01);
(Continued)

(58) Field of Classification Search
None
See application file for complete search history.

(56) References Cited

U.S. PATENT DOCUMENTS 5,152,776 A * 10/1992 Pinchuk ................... 606/192
5,879,357 A     3/1999 Heaton et al.
(Continued)

FOREIGN PATENT DOCUMENTS

JP    07-313515     12/1995
JP    2004-154548    6/2000
(Continued)

OTHER PUBLICATIONS

PCT International Search Report and Written Opinion for PCT/US06/36585; Applicant: Calypso Medical Technologies, Inc.; dated Jun. 23, 2008; ISA/US; 8 pgs.
(Continued)

*Primary Examiner* — Long V Le
*Assistant Examiner* — Bradley Impink
(74) *Attorney, Agent, or Firm* — Perkins Coie LLP

(57) ABSTRACT

Apparatuses and methods for implanting objects, such as a marker, in the lungs of patients. In one embodiment, a bronchoscopic catheter assembly for implanting an object in the lung of a patient includes a handle, a delivery catheter projecting outwardly from the handle, and a push wire contained within the catheter In one aspect of this embodiment, the catheter can be configured to releasably hold a plurality of markers at a distal end. In another aspect of this embodiment, the push wire can be operably connected to the handle and axially moveable within the delivery catheter to eject the marker out of the catheter within the bronchi of the patient. In a further aspect of this embodiment, the marker can further include an anti-migration device associated with the marker for holding the marker in place once the marker is deployed in the bronchi. The anti-migration device can be integral with the marker or positioned proximate to the marker to prevent migration of the marker.

10 Claims, 18 Drawing Sheets

(51) Int. Cl.
| | | |
|---|---|---|
| *A61B 19/00* | (2006.01) | |
| *A61B 1/267* | (2006.01) | |
| *A61B 17/00* | (2006.01) | |
| *A61N 5/10* | (2006.01) | |
| *A61B 17/12* | (2006.01) | |

(52) U.S. Cl.
CPC ..... *A61B17/12104* (2013.01); *A61B 17/12172* (2013.01); *A61B 19/56* (2013.01); *A61B 2017/00809* (2013.01); *A61B 2019/207* (2013.01); *A61B 2019/5251* (2013.01); *A61B 2019/547* (2013.01); *A61B 2019/5454* (2013.01); *A61B 2019/5487* (2013.01); *A61B 2019/562* (2013.01); *A61N 2005/1009* (2013.01)

(56) References Cited

U.S. PATENT DOCUMENTS

| | | |
|---|---|---|
| 6,405,072 B1 | 6/2002 | Cosman |
| 6,702,780 B1 | 3/2004 | Gilboa et al. |
| 6,961,405 B2 | 11/2005 | Scherch |
| 7,280,863 B2 | 10/2007 | Shachar |
| 7,318,805 B2 | 1/2008 | Schweikard et al. |
| 8,239,005 B2 | 8/2012 | Wright et al. |
| 2002/0049362 A1 | 4/2002 | Ding |
| 2002/0065455 A1* | 5/2002 | Ben-Haim et al. ............ 600/407 |
| 2002/0188194 A1 | 12/2002 | Cosman |
| 2002/0193685 A1 | 12/2002 | Mate et al. |
| 2003/0002621 A1 | 1/2003 | Hughes et al. |
| 2003/0052785 A1 | 3/2003 | Gisselberg et al. |
| 2003/0070682 A1* | 4/2003 | Wilson et al. ............ 128/207.16 |
| 2003/0088178 A1 | 5/2003 | Owens et al. |
| 2003/0125616 A1 | 7/2003 | Black et al. |
| 2003/0125622 A1 | 7/2003 | Schweikard et al. |
| 2003/0153829 A1 | 8/2003 | Sarin et al. |
| 2003/0212412 A1 | 11/2003 | Dillard et al. |
| 2004/0019274 A1 | 1/2004 | Galloway et al. |
| 2004/0096033 A1 | 5/2004 | Seppi et al. |
| 2004/0123871 A1* | 7/2004 | Wright et al. ............ 128/899 |
| 2004/0124105 A1 | 7/2004 | Seiler et al. |
| 2004/0127787 A1 | 7/2004 | Dimmer et al. |
| 2004/0133101 A1 | 7/2004 | Mate et al. |
| 2004/0158146 A1 | 8/2004 | Mate et al. |
| 2004/0162574 A1 | 8/2004 | Viola |
| 2005/0085710 A1 | 4/2005 | Earnst et al. |
| 2005/0152495 A1 | 7/2005 | Hesse |
| 2005/0154283 A1 | 7/2005 | Wright et al. |
| 2005/0154293 A1* | 7/2005 | Gisselberg et al. ............ 600/420 |
| 2005/0195084 A1 | 9/2005 | Dimmer et al. |
| 2005/0234332 A1 | 10/2005 | Murphy |
| 2005/0251111 A1* | 11/2005 | Saito et al. ............ 606/1 |
| 2005/0261570 A1 | 11/2005 | Mate et al. |
| 2006/0052694 A1 | 3/2006 | Phillips et al. |
| 2006/0058648 A1 | 3/2006 | Meier et al. |
| 2006/0063999 A1 | 3/2006 | Herron et al. |
| 2006/0074301 A1 | 4/2006 | Meier et al. |
| 2006/0074302 A1 | 4/2006 | Meier et al. |
| 2006/0078086 A1 | 4/2006 | Riley et al. |
| 2006/0079764 A1* | 4/2006 | Wright et al. ............ 600/431 |
| 2006/0093089 A1* | 5/2006 | Vertatschitsch et al. ........ 378/65 |
| 2006/0100509 A1 | 5/2006 | Wright et al. |
| 2007/0106108 A1 | 5/2007 | Hermann et al. |
| 2007/0161884 A1 | 7/2007 | Black et al. |
| 2008/0226149 A1 | 9/2008 | Wischmann et al. |
| 2009/0216150 A1 | 8/2009 | Reichel et al. |

FOREIGN PATENT DOCUMENTS

| | | |
|---|---|---|
| JP | 2001-008947 | 1/2001 |
| WO | WO 96/08208 | 3/1996 |
| WO | WO 9712553 | 4/1997 |
| WO | WO 9830166 | 7/1998 |
| WO | WO 9838908 | 9/1998 |
| WO | WO 9840026 | 9/1998 |
| WO | WO 9927839 | 6/1999 |
| WO | WO 9930182 | 6/1999 |
| WO | WO 9933406 | 7/1999 |
| WO | WO 9940869 | 8/1999 |
| WO | WO 9958044 | 11/1999 |
| WO | WO 9958065 | 11/1999 |
| WO | WO-00/38579 A2 | 7/2000 |
| WO | WO-00/51514 A1 | 9/2000 |
| WO | WO 0051514 | 9/2000 |
| WO | WO 0065989 | 11/2000 |
| WO | WO 0239917 | 5/2002 |
| WO | WO 0239918 | 5/2002 |
| WO | WO 03/053270 | 7/2003 |
| WO | WO 2005067563 | 7/2005 |

OTHER PUBLICATIONS

Sharp et al., "Prediction of Respiratory Tumour Motion for Real-Time Image-Guided Radiotherapy," Published Jan. 16, 2004; IPO Publishing Ltd.; pp. 425-440.

P.G. Seiler, et al., A novel tracking technique for the continuous precise measurement of tumour positions in confomral therapy, Jun. 7, 2000, IOP Publishing Ltd., Phys. Med. Biol., vol. 45, pp. N103-N110.

Seppenwoolde et al, Precise and real-time measurement of 3D tumor motion in lung due to breathing and heartbeat, measured during radiotherapy, Int. J. Radiat. Oncol. Biol. Phys. Jul. 15, 2002, 53, pp. 822-834.

Beyer, Thomas et al. "Dual-modality PET/CT Imaging: the effect of respiratory motion on combined image quality in clinical oncology." European journal of nuclear medicine and molecular imaging 30.4 (2003): 588-596.

Low, Daniel A., et al. "A method for the reconstruction of four-dimensional synchronized CT scans acquired during free breathing." Medical physics 30.6 (2003) 1254-1263.

Wolthaus, J. W. H., et al. "Fusion of respiration-correlated PET and CT scans: correlated lung tumour motion in anatomical and functional scans." Physics in medicine and biology 50.7 (2005): 1569.

* cited by examiner

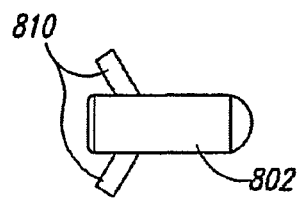
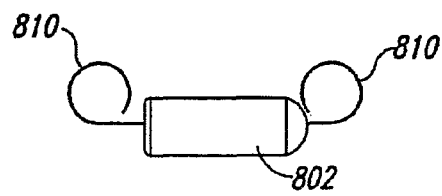
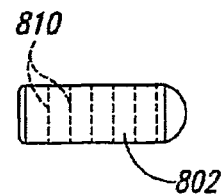
Fig. 13A  Fig. 13B  Fig. 13C
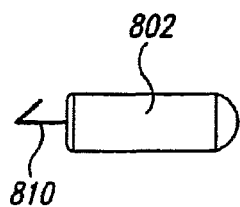
Fig. 13D  Fig. 13E
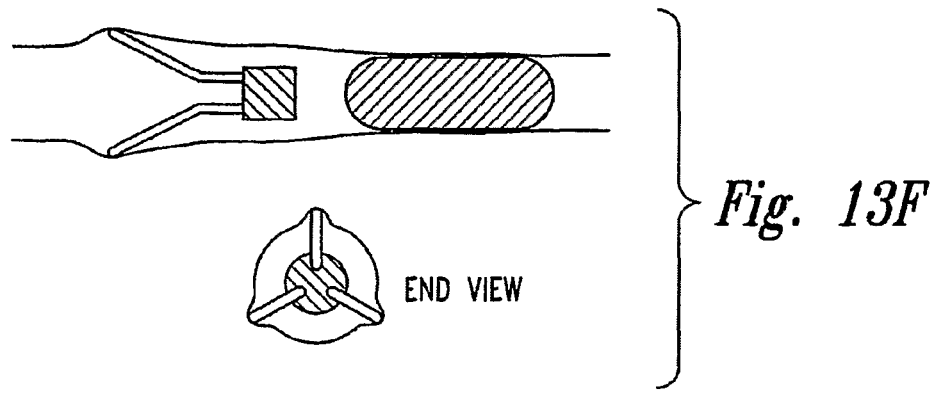
END VIEW
Fig. 13F

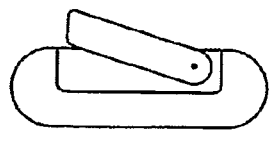
*Fig. 13R*
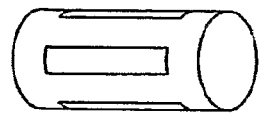
*Fig. 13S*
*Fig. 13T*
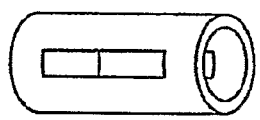
*Fig. 13U*
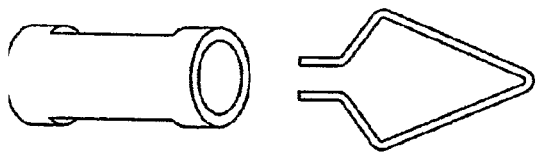
*Fig. 13V*
*Fig. 13W*
*Fig. 13X*
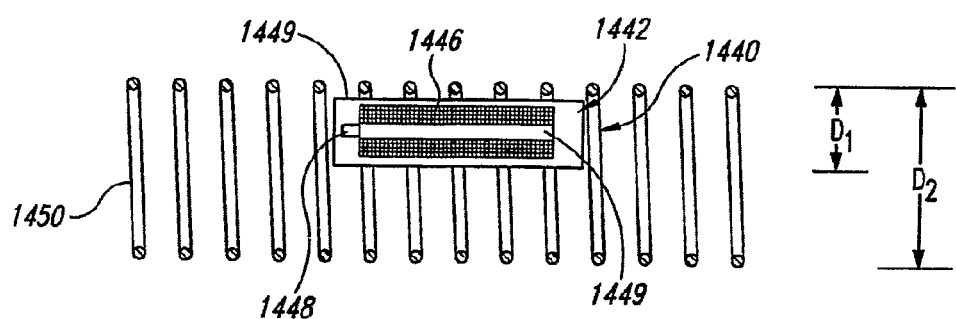
*Fig. 14A*

APPARATUS AND METHODS FOR IMPLANTING OBJECTS, SUCH AS BRONCHOSCOPICALLY IMPLANTING MARKERS IN THE LUNG OF PATIENTS

CROSS-REFERENCE TO RELATED APPLICATION(S)

The present application claims the benefit to U.S. Patent Application No. 60/718,460 filed on Sep. 19, 2005 and U.S. Patent Application No. 60/833,931 filed on Jul. 28, 2006, both which are incorporated herein in their entirety.

TECHNICAL FIELD

The present invention is directed toward bronchoscopically implanting markers in the lung of a patient and more particularly, toward pre-loading a delivery catheter with a marker wherein the marker includes an anti-migration device.

BACKGROUND

Radiation therapy has become a significant and highly successful process for treating prostate cancer, lung cancer, brain cancer and many other types of localized cancers. Radiation therapy procedures generally involve (a) planning processes to determine the parameters of the radiation (e.g., dose, shape, etc.), (b) patient setup processes to position the target at a desired location relative to the radiation beam, (c) radiation sessions to irradiate the cancer, and (d) verification processes to assess the efficacy of the radiation sessions. Many radiation therapy procedures require several radiation sessions (i.e., radiation fractions) over a period of approximately 5-45 days.

To improve the treatment of localized cancers with radiotherapy, it is generally desirable to increase the radiation dose because higher doses are more effective at destroying most cancers. Increasing the radiation dose, however, also increases the potential for complications to healthy tissues. The efficacy of radiation therapy accordingly depends on both the total dose of radiation delivered to the tumor and the dose of radiation delivered to normal tissue adjacent to the tumor. To protect the normal tissue adjacent to the tumor, the radiation should be prescribed to a tight treatment margin around the target such that only a small volume of healthy tissue is irradiated. For example, the treatment margin for prostate cancer should be selected to avoid irradiating rectal, bladder and bulbar urethral tissues. Similarly, the treatment margin for lung cancer should be selected to avoid irradiating healthy lung tissue or other tissue. Therefore, it is not only desirable to increase the radiation dose delivered to the tumor, but it also desirable to mitigate irradiating healthy tissue.

One difficulty of radiation therapy is that the target often moves within the patient either during or between radiation sessions. For example, tumors in the lungs move during radiation sessions because of respiration motion and cardiac functions (e.g., heartbeats and vasculature constriction/expansion). To compensate for such movement, the treatment margins are generally larger than desired so that the tumor does not move out of the treatment volume. However, this is not a desirable solution because the larger treatment margins may irradiate a larger volume of normal tissue.

Localization and/or tracking of markers, such as gold fiducials or electromagnetic transponders, may enable increased tumor radiation and decreased healthy tissue irradiation. However, localization of implanted gold fiducials is limited by high doses of non-therapeutic imaging radiation, expensive fluoroscopic equipment, subjective image interpretation and poor implant stability.

Another challenge in radiation therapy is accurately aligning the tumor with the radiation beam. Current setup procedures generally align external reference markings on the patient with visual alignment guides for the radiation delivery device. For an example, a tumor is first identified within the patient using an imaging system (e.g., X-ray, computerized tomography (CT), magnetic resonance imaging (MRI), or ultrasound system). The approximate location of the tumor relative to two or more alignment points on the exterior of the patient is then determined. During setup, the external marks are aligned with a reference frame of the radiation delivery device to position the treatment target within the patient at the beam isocenter of the radiation beam (also referenced herein as the machine isocenter). Conventional setup procedures using external marks are generally inadequate because the target may move relative to the external marks between the patient planning procedure and the treatment session and/or during the treatment session. As such, the target may be offset from the machine isocenter even when the external marks are at their predeteremined locations for positioning the target at the machine isocenter. Reducing or eliminating such an offset is desirable because any initial misalignment between the target and the radiation beam will likely cause normal tissue to be irradiated. Moreover, if the target moves during treatment because of respiration, organ filling, or cardiac conditions, any initial misalignment will likely further exacerbate irradiation of normal tissue. Thus, the day-by-day and moment-by-moment changes in target motion have posed significant challenges for increasing the radiation dose applied to patients.

Conventional setup and treatment procedures using external marks also require a direct line-of-sight between the marks and a detector. This requirement renders these systems useless for implanted markers or markers that are otherwise in the patient (i.e., out of the line-of-sight of the detector and/or the light source). Thus, conventional optical tracking systems have many restrictions that limit their utility in medical applications. Thus, there is a continuing need for improved localization and tracking of markers, including an improved method of placing the marker and an improved system of preventing movement of the marker once placed.

Tumor target localization has been demonstrated utilizing implanted markers such as gold fiducials (balls and cylinders) and electromagnetic transponders. One method of placement for these markers in the lung is to deliver them into the bronchus/ bronchioles of the lung and then force-fit the markers into the appropriate diameter bronchiole near the treatment target location. The implant location that permits a force-fit of the markers is likely not the most desired location, but one that simply accommodates the force fit. Additionally, the act of breathing, which effects a small enlargement/contraction cycle of the bronchioles, may dislodge the marker from its desired location. Many inhaled drugs also effect changes in the diameter of the bronchioles. Further, actions such as coughing, which typically originate in the alveolar structures near the lung periphery, serve to force the markers from their desired locations to locations closer to the trachea.

Thus implanted marker usage for localization and tracking of lung tissue targets has proven challenging due to marker migration issues. Since markers are surrogates for the actual treatment target position, there is a need to minimize potential for marker migration throughout the entire course of radiation therapy (from treatment planning to last radiation fraction application). Initial positioning and maintenance of marker location should desirably be accomplished independent of bronchus/brochiole size. The position of the marker needs to remain stationary regardless of feature changes within the bronchioles. A multiplicity of devices, methods, and systems are listed to accomplish that task.

The airways in the lungs anatomically constitute an extensive network of conduits that reach all lung areas and lung tissues. Air enters the airways through the nose or mouth, travels through the trachea and into the bronchi and bronchioli of the lunch. The lungs are covered by a think membrane called the pleura. Because of these physiological characteristics of the airways, a marker placed in bronchi and bronchioli may cause pneumothorax when implanted, thus, there is a need for a new and improved device, system, and method for implanting a marker in the region proximate to a tumor or other lesion in the lung.

One recent method for locating a target implanted within the body includes a wireless implantable marker configured to be implanted surgically or percutaneously into a human body relative to a target location. The markers include a casing and a signal element in the casing that wirelessly transmits location signals in response to an excitation energy. One concern of using implanted markers in soft tissues, bronchi or bronchioli is that the markers may move within the patient after implantation. To resolve this concern, Calypso Medical Technologies, Inc. previously developed several anchors and fasteners for securing the markers to soft tissue structures, as disclosed in U.S. application Ser. No. 10/438, 550, which is incorporated herein by reference. Although these anchors may work for percutaneous or surgical implantation, they may be improved for bronchoscopic applications. Therefore, it would be desirable to further develop markers for bronchoscopic deployment and implantation.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 14A is a cross-sectional view of a marker and an anchor in accordance with an embodiment of the invention.

DETAILED DESCRIPTION

Figure 1A:
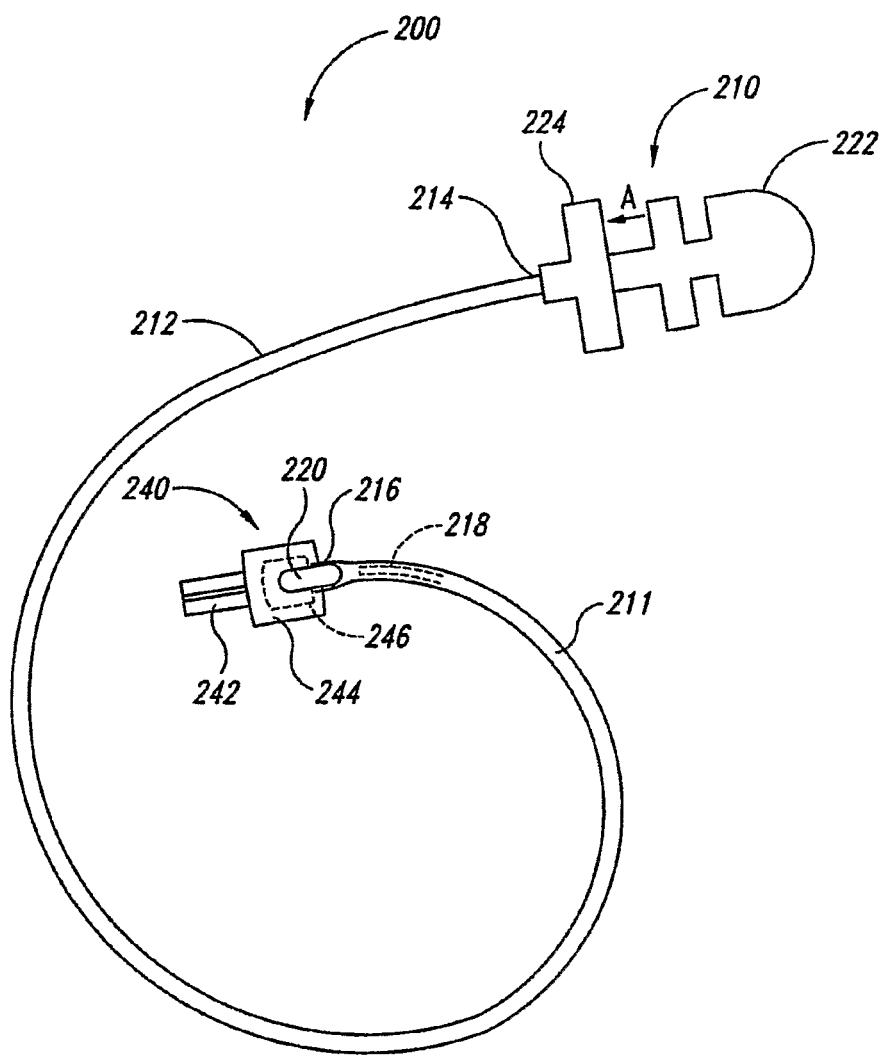
FIGS. 1A-1D are isometric views of exemplary bronchoscopic catheter assemblies in accordance with embodiments of the invention.

In the following description, certain specific details are set forth in order to provide a thorough understanding of various embodiments of the invention. However, one skilled in the relevant art will recognize that the invention may be practiced without one or more of these specific details, or with other methods, components, materials, etc. In other instances, well-known structures associated with the system, the bronchoscope catheter assembly, the marker, the anti-migration device and/or the storage device have not been shown or described in detail to avoid unnecessarily obscuring descriptions of the embodiments of the invention.

Several embodiments and features of a bronchoscopic catheter assembly, a marker or a marker with anchors in accordance with embodiments of the invention are set forth and described in the Figures. In other embodiments of the invention, the markers can include additional or different features than those shown in the Figures. Additionally, several embodiments of markers in accordance with the invention may not include all the features shown in these Figures. For the purposes of brevity, like reference numbers refer to similar or identical components of the markers in the Figures. Additionally, throughout the specification, claims, and drawings, the term "proximal" means nearest the trachea, and "distal" means nearest the alveoli.

The headings provided herein are for convenience only and do not interpret the scope or meaning of the claimed invention.

A. Overview

The following disclosure describes several embodiments of wireless markers configured to be implanted and anchored within the lung of a human in a manner that prevents the markers from migrating from the implantation site. The marker is configured to reduce pneumothorax and may further be configured to include an anchor or anti-migration device.

According to aspects of the invention, a bronchoscopic catheter assembly includes a marker pre-loaded at a distal end of a delivery catheter for bronchoscopically implanting the marker in peripheral airways of the lung. According to further aspects of the invention, a marker storage and loading device for retaining the marker prior to loading in the distal end of the delivery catheter is provided. The marker can extend a selected distance beyond the distal end of the delivery catheter to provide a leading end. According to aspects of the invention, the marker is configured at the leading end to reduce pneumothorax. According to further aspects of the invention, the marker includes an integral anti-migration or anchoring device for preventing migration of the marker after placement of the marker in the lung. According to still further aspects of the invention, an anti-migration device is separate from the marker and positioned adjacent to the deployed marker to prevent migration of the marker in the lung after placement. According to still further aspects of the invention, the marker is shaped and sized to reduce migration.

According to aspects of the invention, a marker for use in the bronchoscopic catheter assembly for localizing a target of a patient comprises a casing, a magnetic transponder at least partially received in the casing, and an anchor carried by the casing. The casing is a biocompatible barrier configured to be implanted in the patient. The casing can be a generally cylindrical capsule that is sized to fit within a catheter or a bronchoscope for bronchoscopic implantation, but the casing can have other geometric shapes, sizes, and configurations in other applications. For example, the casing can be larger for implanting the marker in the bronchus. The magnetic transponder produces a wirelessly transmitted magnetic field in response to a wirelessly transmitted excitation energy. The magnetic transponder can further comprise a magnetic core, a coil wrapped around the core, and a capacitor coupled to the coil. The anchor, which can project from the casing, be integral to the casing, or be independent from the casing, secures the marker to an anatomical structure once the marker has been deployed from the bronchoscopic catheter assembly to prevent the marker from moving from the implantation site. According to aspects, the anchor may be detached from the marker. In another embodiment, the marker may be secured to the anatomical structure by mechanical members or chemical attributes.

According to further aspects, an anchorable marker configured for bronchoscopic implantation for localizing a target of a patient comprises a casing, a transponder that produces a wirelessly transmitted magnetic field in response to a wirelessly transmitted excitation field, and an anchor partially embedded within the casing. The anchor can further be configured for bronchoscopic implantation and have a shape and/or material that pierces, engages or otherwise interfaces with the anatomical anchoring site such that the marker cannot be easily dislodged. Alternatively, the casing is shaped to reduce migration of the marker, for example, the casing may be wedge shaped, include a hook, or have a surface texture.

The invention further includes methods for manufacturing and using markers with anchors. One embodiment of such a method comprises providing a transponder that produces a wirelessly transmitted magnetic field in response to a wirelessly transmitted excitation field and forming a casing around the transponder. This method can further include embedding, attaching or forming an anchor in the casing. In alternative embodiments, the anchor can be detached from the marker. In further embodiments, the casing may be the anchor.

According to one current practice, the marker is forcibly wedged into the lumen, however, this will work only for limited settings and circumstances. The marker must be approximately the same size as the lumen at the desired geographic placement location. The luminal wall must possess the appropriate elastic characteristics to retain the force-fitted marker. Forces such as those caused by coughing and wheezing serve to dislodge the marker. Potentially, mucous transport systems in the bronchioles could dislodge a force-fit marker. Inhaled drugs may serve as broncho-dilators and broncho-constrictors. Further, tumor shrinkage during radiation therapy, diaphragmatic motion, the movement of air, and the various pressure profiles within the lung may serve to dislodge a positional marker.

Human lungs are located on either side of the heart and occupying a large portion of the chest cavity from the collarbone to the diaphragm. The lungs are covered by a thin membrane called the pleura. Air travels to the chest cavity through the trachea, which divides into two bronchi, each of which enters a lung. The bronchi divide and subdivide into a network of countless tubules. The smallest tubules, or bronchioles, enter cup-shaped air sacs known as alveoli, which number about 700 million in both lungs. In the case of a marker that is force-fit into a bronchiole, given that bronchioles decrease in diameter toward the lung periphery, any marker dislodgement would typically result in the marker moving toward the trachea, since there is no mechanism to force the marker further into the decreasing diameter lumen. So, in the case of a force fit marker, a solitary secondary plug could serve to secure the marker in place. Feasibly, since the marker should not move further down the bronchiole structure due to its decreasing luminal diameter, the secondary securing device would need to provide only a marginal increase in holding capacity to keep the marker in place. It should be noted that in this case, since the retention device is located on the side closer to the trachea side, it will be located in a diameter that is incrementally larger than that of the marker location.

Dependant upon the specific elastic properties at any specific bronchial location, a plurality of devices and methods exist for entrapping a marker in the bronchial lumen. A LRD (luminal retention device) embodied as a plug can be force fit into a tubular structure such as a bronchus, or other bodily lumen, to trap or hold in place a marker. A LRD rigid plug would rely on the resiliency of the lumen to hold the plug in place, while a plug constructed of silicone, sponge, or other similar materials would inherently possess its own resiliency. The fibrin-thrombin type adhesives and adhesive blobs could be used to a) build a LRD plug in-place in the lumen to prevent the marker from dislodging, b) augment the diameter or attach a smaller sized LRD plug to the luminal wall, or c) used to glue the transponder directly to the wall. Cyanoacrylate adhesives could be used in this application as well. A related product, the foamed-matrix biologically-based materials possess mechanical properties similar to weak plastics prior to being exposed to body fluids, and could be pre-formed into acceptable shapes to force-fit into a lumen, but would shortly form a soft, biologically based plug once established in the mucous of the bronchial tree.

Many shapes can be utilized as an LRD anchor or plug, since the goal is to fixate the marker. Materials many include plastics, metals, adhesives, expandable sponges, and bio-materials (e.g. collagen, connective tissue derivatives). Additional embodiments include: wire or shaped metal "ring", hex, umbrella, etc. A form resembling a helical shaped wire spring can be advanced through a small diameter conduit to the desired location in a compressed state, expanding to the luminal diameter upon expulsion from the confines of the conduit, trapping the marker on one side. A plurality of materials could be utilized, including, at least, metals, plastics, and matrix materials such as carbon-fiber.

Further, the internally-springed, radially self-expander marker anchor allows for diametral growth or shrinkage of the lumen in which it resides, without requiring adjustment or positioning. While the device has been presented herein as a single anchor, it may be used in pairs within a lumen to trap a marker between the pair of anchors. As long as the marker cannot escape through the LRD device toward to the larger bronchiole structures the device should remains stationary and the goal will be realized.

Consideration should be allowed for delivery of any of the devices as well. The ability of a device to be delivered in a compact, or compressed state, is a definite advantage. Further, the ability of a device to compensate for differences in lumen size and elasticity allows the use of a single device for a plurality of lumen sizes and, therefore, lumen locations. To fixate a marker within a lumen, the marker can be forcibly wedged within the lumen, anchored to the luminal wall, entrapped against the luminal wall, anchored to the luminal wall using a leg of a bifurcation point, entrapped within the lumen by a second device, or trapped at a specific location within the lumen by the use of two secondary devices. Combinations of these methods may be employed as well.

B. Catheter Having a Preloaded Marker Positioned at a Distal End

Figure 1B:
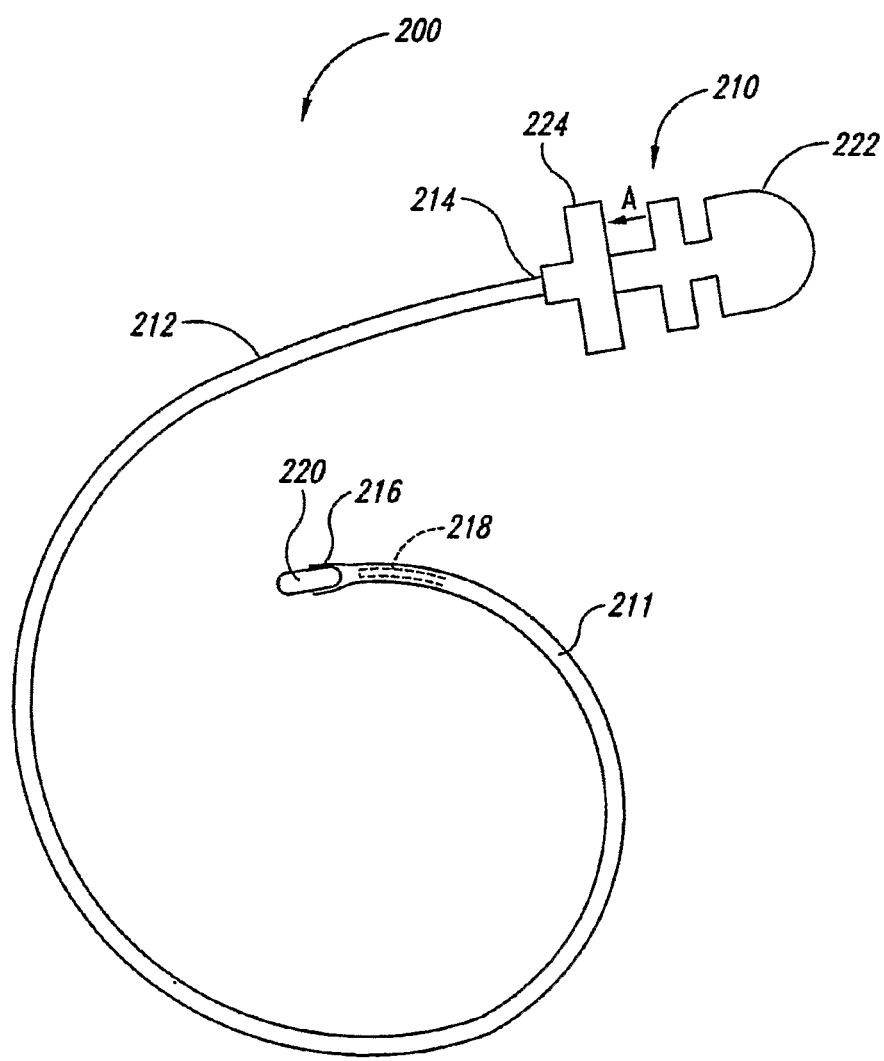

FIG. 1A is an isometric view of a bronchoscopic catheter assembly 200 for use in a working channel of a bronchoscope (not shown for clarity) and a storage and loading device 240 attached to a distal end 216 of a delivery catheter 212 in accordance with an embodiment of the invention. FIG. 1B is an isometric view of the bronchoscopic catheter assembly 200 of FIG. 1A with a marker 220 loaded in the distal end 216 of the delivery catheter 212 and the storage and loading device 240 removed. As shown in FIGS. 1A and 1B, the bronchoscopic catheter assembly 200 includes a delivery catheter 212 having a deployment channel 211 configured to releasably retain a marker 220 at a distal end 214 of the delivery catheter 212 such that the marker 220 extends a selected distance beyond a distal end 216 of the delivery catheter 212.

Referring now to FIG. 1A, the storage and loading device 240 for retaining the marker 220 prior to loading in the distal end 216 of the delivery catheter 212 is provided. The storage and loading device 240 includes a receiving chamber 246 for releasably retaining a marker 220. The storage and loading device 240 can include a stem 242 which is configured to be held by the hand of an operator, and can further include a housing 244 contained around the storage chamber 246. The housing 244 additionally provides an alignment means for mating with the distal end of the catheter when loading the marker 220 into the catheter as discussed further with respect to FIG. 5.

Referring now to FIG. 1B, a proximatal end 214 of the delivery catheter 212 is configured to engage a handle 210 having an actuator 222. The actuator 222 is moveable between a first position and a second position along arrow A. In the second position, the actuator 222 abuts a flange 224. The flange 224 is configured to stop movement of the actuator 222 along line A by engaging the actuator 222 on a first side. On a second side, opposite the first side, the flange 224 retains the delivery catheter 212. The flange 224 further includes a sleeve 214 for slidably receiving a push wire 218 therein.

The push wire 218 is retained by and moves with the actuator 222. The push wire 218 may be a Teflon wire, steel cable, steel wire, or other flexible cable having sufficient rigidity to deploy the marker 220 when the actuator 222 is moved along line A. As shown in FIG. 3B, the push wire 218 may include a disc shaped end 404 for engaging the marker 220. Alternatively, an end 404 of the push wire 218 may be an appropriately shaped wire or rod. The end 404 may have a diameter dimension slightly less than the diameter dimension of the channel 211 to allow the push wire 218 to slide co-axially therein.

Figure 2A:
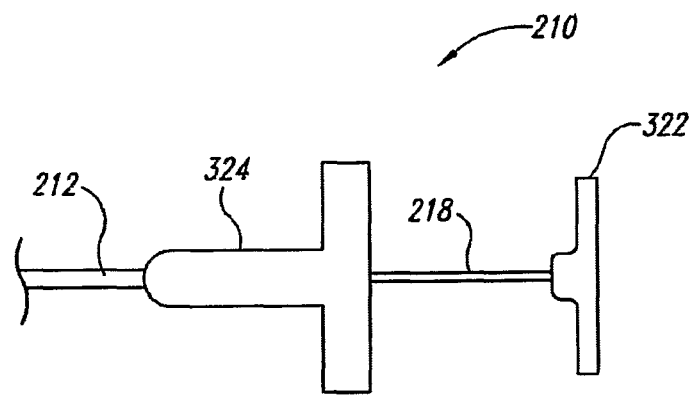
FIGS. 2A and 2B are isometric views of a bronchoscopic catheter handle having an actuator and a housing in accordance with embodiments of the invention.
Figure 2B:
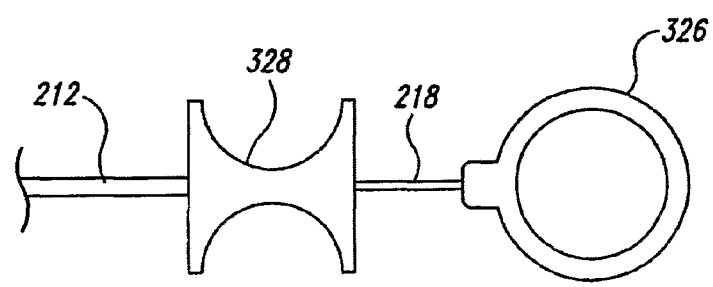

The handle 210 is configured to be moveable by an operator (not shown) and may further be configured to attach to the working channel of the bronchoscope. Referring now to FIGS. 2A and 2B, the handle 210 can include an actuator 322 including a button or flat plate configured to be engaged by a digit of an operator's hand (not shown for purposes of clarity). The actuator 322 abuts the housing 324 to stop axial movement along line A. Alternatively, the handle 210 can include an actuator 326 including a ring configured to be engaged by a digit of an operator's hand. As shown in FIG. 2B, the housing 326 can be ergonomically shaped to the hand of a user. Alternative configurations of the actuator can further be provided.

Figure 1C:
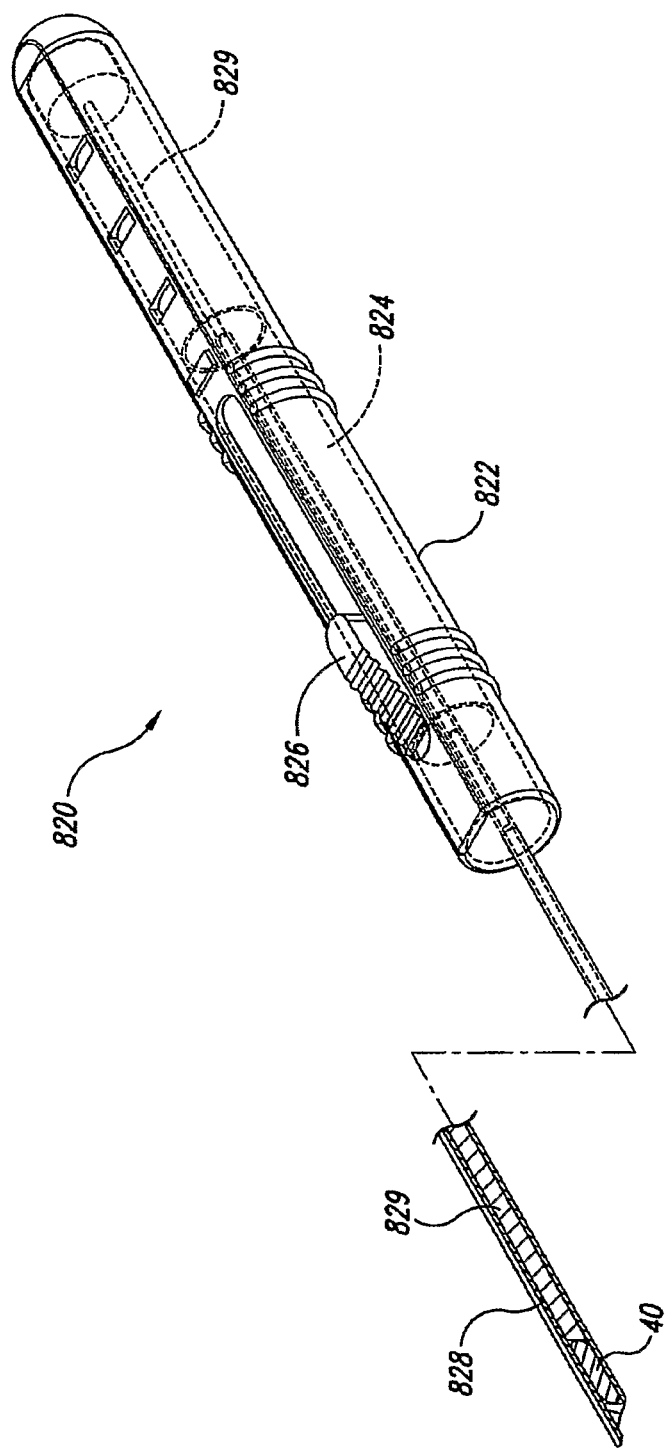

One aspect of several embodiments of the present invention is delivering or deploying the markers 40 into or at least proximate to a tumor located in the lung of the patient. FIG. 1C is a cross-sectional view of a delivery device 800 for deploying a marker 40 in the patient. The delivery device 800 can be a bronchoscope, catheter, or other device configured to pass through a lumen in the respiratory system of the patient. The delivery device 800 includes a handle 802 and an elongated body 804 attached to the handle 802. More specifically, the elongated body 804 includes a proximal section 806 at the handle 802 and a distal section 808 configured to pass through lumen in the respiratory system. In many embodiments, the distal section 808 of the elongated body 804 is flexible, but in other embodiments the entire elongated body can be flexible or rigid. The marker 40 is supported by the elongated body 804 at the distal section 808 for deployment into the patient. In several embodiments, the delivery device 800 further includes a deployment mechanism 810 that is operable from the handle 802 to release the marker 40 into the patient. The deployment mechanism 810 can be a push rod that pushes the marker 40 out of the distal section 808 of the elongated body 804. In an alternative embodiment, the deployment mechanism 810 can include a cannula and a stylet slidably received in the cannula. In this embodiment, the cannula and stylet are configured to move together to project distally beyond the distal section 808 of the elongated body 804, and then the cannula may be withdrawn proximally relative to the stylet to release the marker into the patient. Analogous embodiments of cannulas and stylets that can be used with the delivery device 800 are described below with respect to FIG. 1D.

The delivery device 800 can further include a steering mechanism 812 that is operable from the handle 802. The steering mechanism 812 can include an attachment point at the distal section 808 and a slidable member 814 configured to move longitudinally relative to the elongated body 804. Longitudinal movement of the slidable member 814 flexes the distal section 808 in a manner that steers the delivery device 800 through bends and bifurcations in the lumen of the respiratory system. In other embodiments, the steering mechanism comprises a flexible support element and a flexible control element attached to the flexible support element such that tension applied to the control element flexes the flexible support element. Suitable steering mechanisms are set forth in U.S. Pat. No. 6,702,780 and U.S. Patent Application Publication No. US 2003/0208101 A1, both of which are incorporated herein by reference.

Figure 1D:
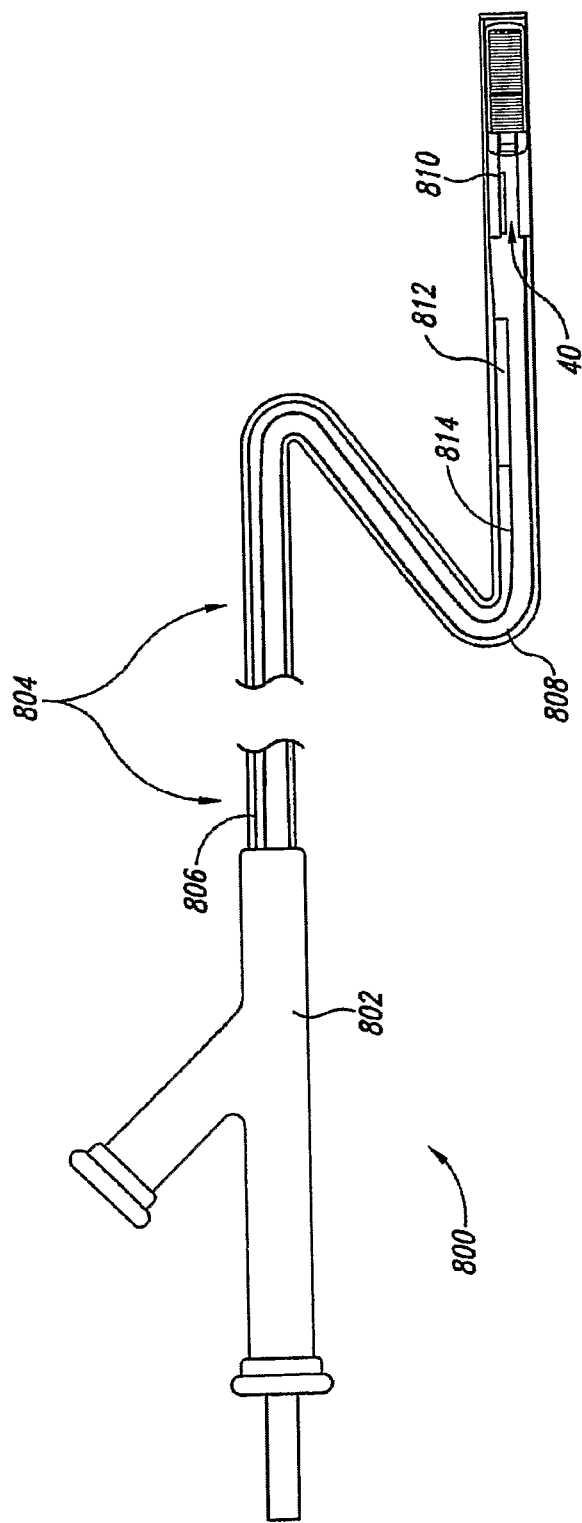

FIG. 1D is an isometric view of a delivery device 820 in accordance with another embodiment of the invention. The delivery device 820 can be a needle or other type of introducer for percutaneously implanting the marker 40 into the lung of the patient trans-thoracically. The delivery device 820 includes a handle 822, a slider 824 received in the handle 822, and an actuator 826 attached to the slider 824. The delivery device 820 further includes a cannula 828 attached to the slider 824 and a stylet 829 fixedly attached to the handle 822. In operation, the cannula 828 and stylet 829 are percutaneously inserted into the patient. When the marker 40 is at a desired location relative to the target, the actuator 826 is drawn proximately to move the slider 824 proximally within the handle 822. This motion withdraws the cannula 828 over the stylet 829 to release the marker 40 in the patient. The delivery device 820 and several other embodiments of delivery devices for percutaneous implantation of the markers are described in U.S. Patent Application No. 60/590,521 and Ser. No. 10/334,699, both of which are incorporated herein by reference in their entirety.

Figure 3A:
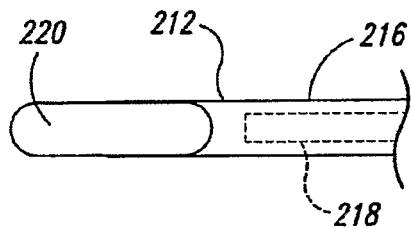
FIGS. 3A-3D are isometric cross-sectional views of the distal end of the delivery catheter including a marker retained therein in accordance with embodiments of the invention.
Figure 3B:
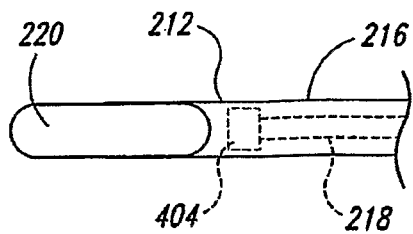
Figure 3C:
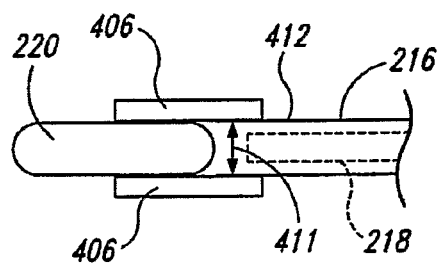

Referring now to FIGS. 3A-3D, the distal end 216 of the delivery catheter 212 releasably retains the marker 220. As shown in FIG. 3A, an outside diameter of the marker 220 can be approximately equal to the diameter of the channel 211. Alternatively, as shown in FIG. 3C, a sleeve 406 can be placed at a distal end 216 of the delivery catheter 412. An inside diameter of the sleeve 406 can be approximately equal to the outside diameter of the marker 220 and configured to releasably retain the marker 220. According to this embodiment, the channel 411 can have an inside diameter smaller than the outside diameter of the marker 220. The sleeve 406 may be made from a semi-rigid, rigid, or flexible material different from the catheter 412, or may be made from the same material as the catheter 412.

Figure 3D:
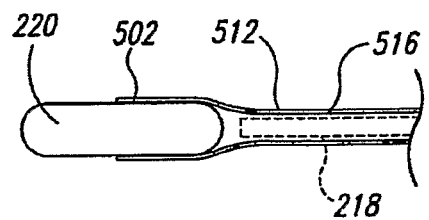

Referring now to FIG. 3D, the distal end 516 of the delivery catheter 512 releasably retains the marker 220 by expanding around the marker 220. According to aspects of this embodiment, the inside diameter of the delivery catheter 512 is less that the outside diameter of the marker 220. The delivery catheter 512 is made from a sufficiently flexible material to allow the delivery catheter 512 to expand around the marker 220 and releasably retain the marker 220 prior to deployment. Alternatively, another method besides compression fit to hold the marker in place is to use a material for example, coconut oil that is solid at room temperature and liquid at body temperature. Alternately, the material could be liquid soluble, such as sucrose or NaCl; exposure to the lumen would detach the marker.

In operation, a bronchoscope is inserted into the nose or mouth of a patient past the vocal chords and into the lungs by threading a distal end through the bronchi. At least one marker is pre-loaded at the distal end 216 of the delivery catheter 212. Once the bronchoscope is positioned relative to the tumor or lesion, the delivery catheter 212 is positioned in the working channel of the bronchoscope such that the distal end 216 of the delivery catheter 212 is at or slightly beyond a distal end of the bronchoscope. Once the delivery catheter 212 is in the desired position, the actuator is engaged, causing the push wire 218 to move axially within the channel and deploy the marker. After at least one marker is deployed, a second marker can be deployed; the catheter can be repositioned prior to deploying a second catheter; the catheter can be removed and the bronchoscope can be removed or repositioned to deploy a second marker; or the catheter can be repositioned to deploy a second marker. According to aspect of the invention, as the marker is deployed from the catheter, an anti-migration device integral to the marker or separate from the marker can further be deployed to retain the marker in a desired position. According to this aspect, the anti-migration device anchors the marker to the anatomical anchoring site as further described below.

According to an alternative embodiment of the present invention, the delivery catheter 212 contains a fluid (not shown) in lieu of or in addition to a push wire. According to aspects of this embodiment, fluid pressure presses out on the catheter in addition to applying pressure to the marker, thus deploying the marker. According to aspects of this embodiment, less longitudinal recoil is experienced due to a minimal force applied longitudinally during deployment. Alternatively, the fluid may occupy the space around the push wire such that the fluid and the push wire are moved forward at the same time by the actuator. According to further aspects of the invention, the fluid contained in the catheter 212 could be an adhesive such that any fluid discharged with the marker deployment would further act as an anti-migration device. Alternatively, the fluid may be a therapeutic compound, for example, an antibiotic, to prevent infection, reduce pain, or facilitate aspects of the procedure.

Figure 4:
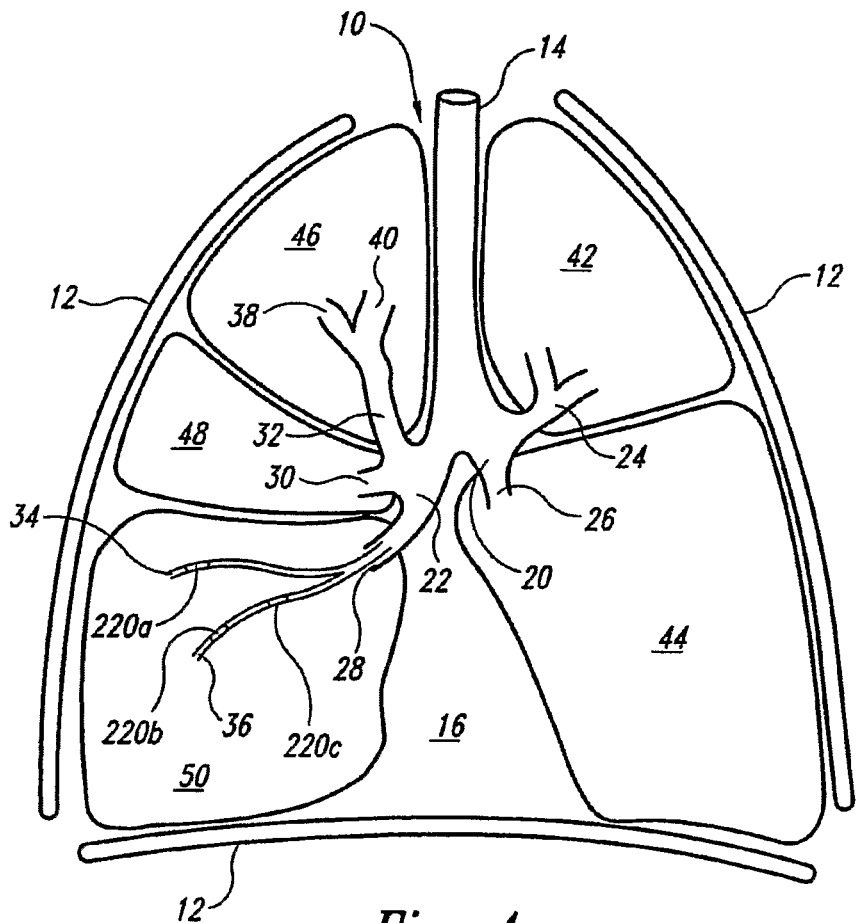
FIG. 4 is a cross-sectional view of a respiratory system having markers implanted therein in accordance with an embodiment of the invention.

FIG. 4 is a cross-sectional view of an exemplary healthy respiratory system 110 having markers 220*a-c* positioned therein. The respiratory system 110 resides within a thorax 16 which occupies a space defined by a chest wall 12 and a diaphragm 13. The respiratory system 10 includes trachea 16; left mainstem bronchus 20 and right mainstem bronchus 22 (primary, or first generation); lobar bronchial branches 24, 26, 28, 30, 32, 38 and 40 (second generation), and segmental branches 34 and 36 (third generation). The respiratory system 10 further includes left lung lobes 42 and 44 and right lung lobes 46, 48 and 50. Each bronchial branch and sub-branch communicates with a different portion of a lung lobe, either the entire lung lobe or a portion thereof. As used herein, the term "passageway" is meant to denote either a bronchi or bronchioli, and typically means a bronchial branch of any generation.

As shown in FIG. 4, three transponders 220*a-c* are positioned in the respiratory system 110 of a patient in the proximity of a tumor or lesion 100. The transponders 220*a-c* are used to localize a patient target treatment isocenter relative to a linear accelerator machine isocenter as described further herein. As a process step during radiation therapy treatment planning, a patient undergoes a CT scan whereby the X, Y, and Z positions of the radiographic centers for all three transponders 220*a-c* as well as the X, Y, and Z position for the treatment target isocenter are identified. To localize a patient treatment target isocenter relative to the linear accelerator treatment target isocenter both prior to and during radiation therapy delivery, the three transponder positions that are positioned in the lung are localized electromagnetically and then used to calculate the position of the treatment target isocenter position and rotational offsets.

The markers 220*a-c* are placed in the respiratory system 110 by the bronchoscopic catheter assembly 200 as described further herein. The markers 220*a-c* are preferably a small alternating magnetic transponder. The transponders can each have a unique frequency relative to each other to allow for time and frequency multiplexing. The transponders can accordingly include a core, a coil wound around the core, and a capacitor electrically coupled to the coil. The bronchoscopic catheter assembly 200 can deploy one or more transponders, and as such is not limited to having three transponders as illustrated. The transponders are localized using a source, sensor array, receiver, and localization algorithm as described further herein.

In operation, the three transponders may be used to localize a treatment target isocenter relative to a linear accelerator radiation therapy treatment isocenter. The treatment target localization may include both translational offset (X, Y, and Z directions) and a rotational offset (pitch, yaw, and roll) relative to a linear accelerator coordinate reference frame.

C. Marker Storage and Loading Device for Use with a Catheter

Figure 5:
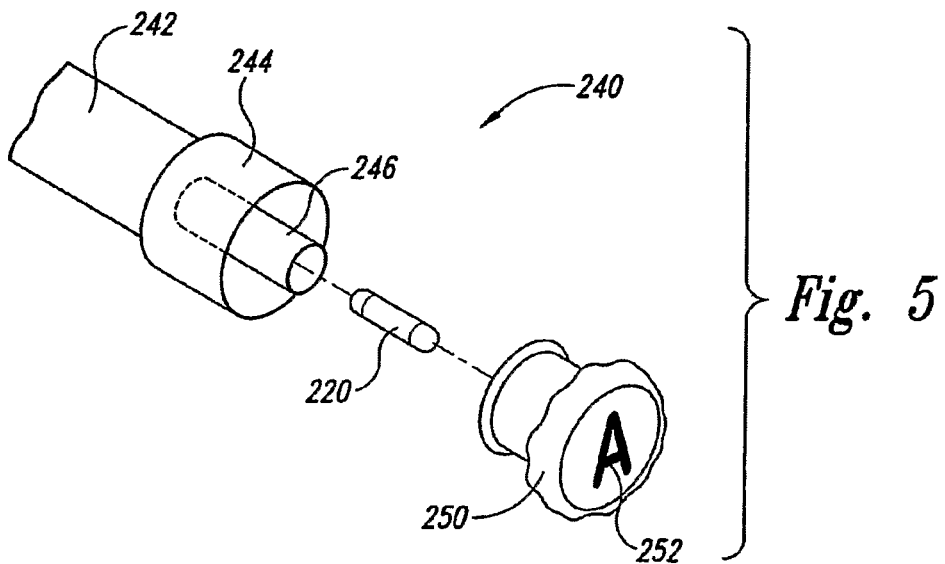
FIG. 5 is an isometric view of a storage and loading transfer capsule in accordance with embodiments of the invention.

Referring now to FIG. 5, a storage and loading device for retaining the marker prior to loading in the distal end of the delivery catheter 212 is provided. The storage and loading device 240 includes a storage chamber 246 for releasably storing a marker prior to loading, and a cap 250. The storage and loading device 240 can include a stem 242 which is configured to be held by the hand of an operator, and can further include a housing 244 contained around the storage chamber 246. The housing 244 additionally provides an alignment means for mating with the distal end 216 of the delivery catheter 212 when loading the marker 220 into the catheter. According to further embodiments of the invention, the housing 244 provides additional surface area for the operator to grip when loading the marker 220 into the distal end 216 of the delivery catheter 212 and can also protect the marker 220 during shipping. According to aspects of the invention, the storage and loading device 240 can be an airtight configuration to provide a sterilized environment for the marker 220 prior to loading into the delivery catheter 212. The storage and loading device 240 can further be constructed of an electromagnetically transparent material to allow the marker 220 to be tested prior to loading. Alternative configurations of the storage and loading device 240 may include, for example, the stem 242 can include a knob, flange, button, or disk in an ergonomic configuration.

According to further aspects of the invention, the cap 250 or other portion of the storage and loading device 240 can include a marking 252 to identify each marker, for example, when the marker is an electromagnetic transponder with a unique frequency. The marking 252 may be a letter, number, color, or other indication to differentiate and/or identify the marker contained in the storage and loading device 240.

In operation, the marker may be first interrogated to confirm identification aspects, such as frequency. Prior to loading the marker 220 into the distal end of the delivery catheter 212, the cap 250 of the storage and loading device 240 is removed, for example, by pulling, twisting or snapping the cap 250 from the housing 244. Once the cap 250 is removed from the housing 246, the housing 244 and the storage chamber 246 are mated with the distal end 216 of the delivery catheter 212 to transfer the marker 220 from the storage chamber 246 to the distal end 216 of the delivery catheter 212. For example, the storage and loading device 240 can push onto the delivery catheter 212; the storage and loading device 240 can then twist to transfer the marker 220 to the distal end 216 of the delivery catheter 212; and the storage and loading device can then be removed from the distal end 216 of the delivery catheter 212.

In operation, the marker may be loaded into the catheter according to various configurations. For example, the anti-migration device may be pre-loaded into catheter at manufacturing site while the marker is pre-loaded just prior to implantation. Alternatively, both the anti-migration device and the marker are pre-loaded into individual catheters at manufacturing site. Additionally, a sterile package may include one or more pre-loaded catheters. In yet another embodiment, both the anti-migration device and the marker may be pre-loaded into the catheter just prior to implantation.

D. Catheter Tip Configured to Reduce Pneumotorax

According to aspects of the invention, a distal end of a catheter is configured to reduce pneumothorax. The marker 220 is pre-loaded into the distal end 216 of the delivery catheter 212 such that a portion of the marker 220 extends beyond the distal end 216 of the delivery catheter 212, thus providing a rounded leading end of the delivery catheter 212. Providing a rounded leading end of the distal end of the delivery catheter 212 by pre-loading a cylindrical shaped marker, such as a transponder, reduces the puncture rate of the visceral pleura which can occur during bronchoscopic implantation, and thus reduces the likelihood of pneumothorax. Without being bound by theory, pre-loading the cylindrical shaped marker provides a rounded end shape to the delivery catheter 212; the rounded end shape keeps the delivery catheter 212 centered in the passageway. The rounded leading end also maximizes the surface area of tissue (e.g. visceral pleura) that the distal end of the catheter contacts. The catheter distal end is thus less likely to cut through tissue since it maximizes tissue surface area contact by incorporating a smooth rounded tip that does not include any edges that could concentrate force facilitate tissue perforation.

E. Radiation Therapy Systems With Real-time Tracking Systems

Figure 6:
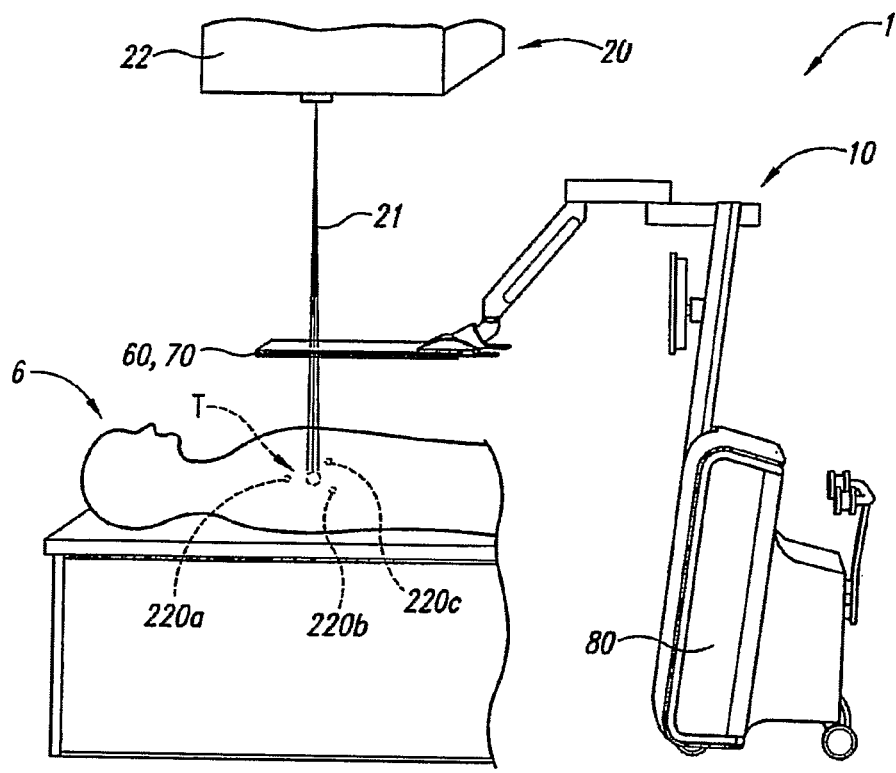
FIG. 6 is an isometric view of a radiation therapy system for applying guided radiation therapy to a target within a lung in accordance with embodiments of the invention.
Figure 7:
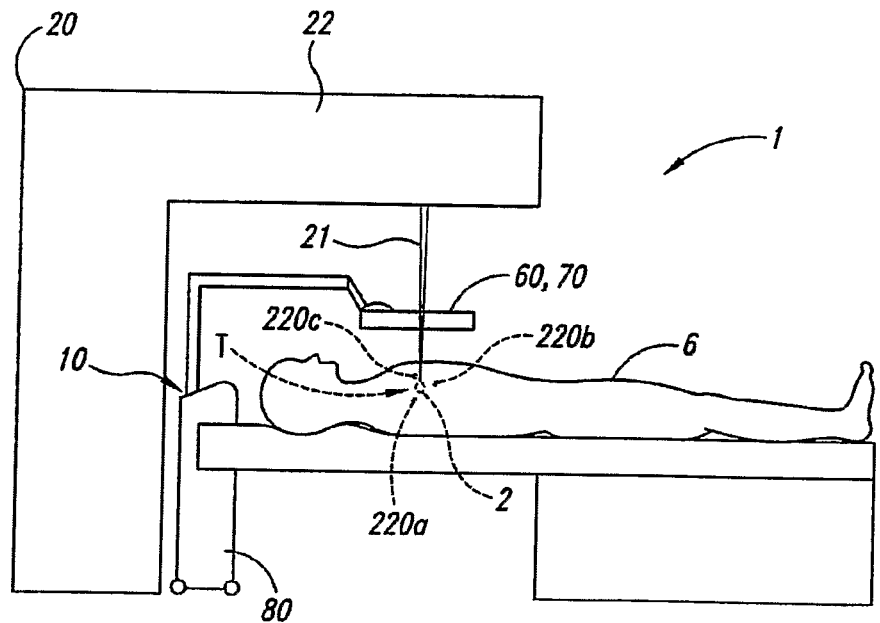
FIG. 7 is an isometric view of a radiation therapy system for applying guided radiation therapy to a target within a lung in accordance with embodiments of the invention.

FIGS. 6 and 7 illustrate various aspects of a radiation therapy system 1 for applying guided radiation therapy to a target 2 (e.g., a tumor) within a lung or other part of a patient 6. The radiation therapy system 1 has a localization system 10 and a radiation delivery device 20. The localization system 10 is a tracking unit that locates and tracks the actual position of the target 2 in real time during treatment planning, patient setup, and/or while applying ionizing radiation to the target from the radiation delivery device. Moreover, the localization system 10 continuously tracks the target and provides objective data (e.g., three-dimensional coordinates in an absolute reference frame) to a memory device, user interface, linear accelerator, and/or other device. The system 1 is described below in the context of guided radiation therapy for treating a tumor or other target in the lung of the patient, but the system can be used for tracking and monitoring other targets within the patient for other therapeutic and/or diagnostic purposes.

The radiation delivery source of the illustrated embodiment is an ionizing radiation device 20 (i.e., a linear accelerator). Suitable linear accelerators are manufactured by Varian Medical Systems. Inc. of Palo Alto, Calif.; Siemens Medical Systems, Inc. of Iselin, N.J.; Elekta Instruments, Inc. of Iselin, N.J.; or Mitsubishi Denki Kabushik Kaisha of Japan. Such linear accelerators can deliver conventional single or multi-field radiation therapy, 3D conformal radiation therapy (3D CRT), IMRT, stereotactic radiotherapy, and tomo therapy. The radiation delivery device 20 can deliver a gated, contoured, or shaped beam 21 of ionizing radiation from a movable gantry 22 to an area or volume at a known location in an external, absolute reference frame relative to the radiation delivery device 20. The point or volume to which the ionizing radiation beam 21 is directed is referred to as the machine isocenter.

The tracking system includes the localization system 10 and one or more markers 220. The localization system 10 determines the actual location of the markers 220 in a three-dimensional reference frame, and the markers 220 are typically within the patient 6. In the embodiment illustrated in FIGS. 6 and 7, more specifically, three markers identified individually as markers 220*a-c* are implanted in the lung of the patient 6 at locations in or near the target 2. In other applications, a single marker, two markers, or more than three markers can be used depending upon the particular application. The markers 220 are desirably placed relative to the target 2 such that the markers 220 are at least substantially fixed relative to the target 2 (e.g., the markers move at least in direct proportion to the movement of the target). As discussed above, the relative positions between the markers 220 and the relative positions between a target isocenter T of the target 2 and the markers 220 can be determined with respect to an external reference frame defined by a CT scanner or other type of imaging system during a treatment planning stage before the patient is placed on the table. In the particular embodiment of the system 1 illustrated in FIGS. 6 and 7, the localization system 10 tracks the three-dimensional coordinates of the markers 220 in real time relative to an absolute external reference frame during the patient setup process and while irradiating the patient to mitigate collateral effects on adjacent healthy tissue and to ensure that the desired dosage is applied to the target.

F. General Aspects of Markers and Localization Systems

Figure 8:
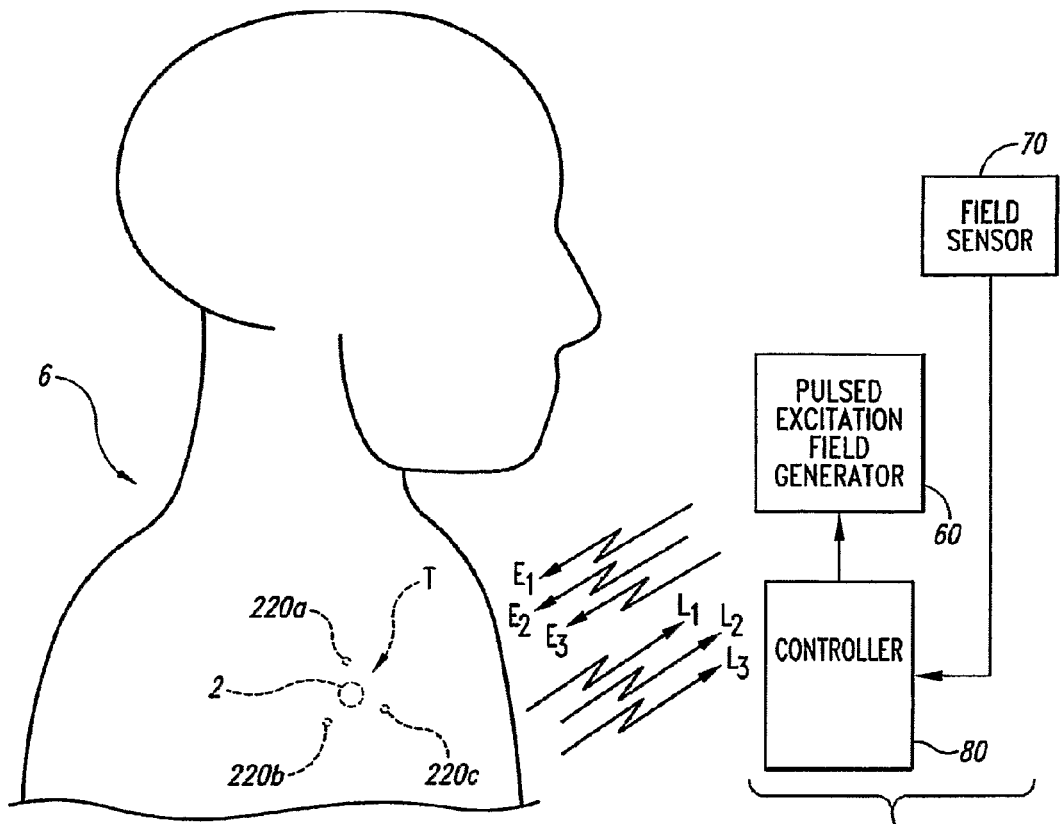
FIG. 8 is a schematic view illustrating the operation of a localization system and markers for treating a tumor or other target in the lung of the patient in accordance with embodiments of the invention.

FIG. 8 is a schematic view illustrating the operation of an embodiment of the localization system 10 and markers 220a-c for treating a tumor or other target in the lung of the patient. The localization system 10 and the markers 220a-c are used to determine the location of the target 2 (FIGS. 6 and 7) before, during, and after radiation sessions. More specifically, the localization system 10 determines the locations of the markers 220a-c and provides objective target position data to a memory, user interface, linear accelerator, and/or other device in real time during setup, treatment, deployment, simulation, surgery, and/or other medical procedures.

In one embodiment of the localization system, real time means that indicia of objective coordinates are provided to a user interface at (a) a sufficiently high refresh rate (i.e., frequency) such that pauses in the data are not humanly discernable and (b) a sufficiently low latency to be at least substantially contemporaneous with the measurement of the location signal. In other embodiments, real time is defined by higher frequency ranges and lower latency ranges for providing the objective data to a radiation delivery device, or in still other embodiments real time is defined as providing objective data responsive to the location of the markers (e.g., at a frequency that adequately tracks the location of the target in real time and/or a latency that is substantially contemporaneous with obtaining position data of the markers).

1. Localization Systems

The localization system 10 includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 220a-c in the patient 6 (FIG. 6). The embodiment of the excitation source 60 shown in FIG. 8 produces a pulsed magnetic field at different frequencies. For example, the excitation source 60 can frequency multiplex the magnetic field at a first frequency E1 to energize the first marker 220a, a second frequency E2 to energize the second marker 220b, and a third frequency E3 to energize the third marker 220c. In response to the excitation energy, the markers 220a-c generate location signals L1-3 at unique response frequencies. More specifically, the first marker 220a generates a first location signal L1 at a first frequency in response to the excitation energy at the first frequency E1, the second marker 220b generates a second location signal L2 at a second frequency in response to the excitation energy at the second frequency E2, and the third marker 220c generates a third location signal L3 at a third frequency in response to the excitation enerqy at the third frequency E3. In an alternative embodiment with two markers, the excitation source generates the magnetic field at frequencies E1 and E2, and the markers 220a-b generate location signals L1 and L2, respectively.

The sensor assembly 70 can include a plurality of coils to sense the location signals L1-3 from the markers 220a-c. The sensor assembly 70 can be a flat panel having a plurality of coils that are at least substantially coplanar relative to each other. In other embodiments, the sensor assembly 70 may be a non-planar array of coils.

The controller 80 includes hardware, software, or other computer-operable media containing instructions that operate the excitation source 60 to multiplex the excitation energy at the different frequencies E1-3. For example, the controller 80 causes the excitation source 60 to generate the excitation energy at the first frequency E1 for a first excitation period, and then the controller 80 causes the excitation source 60 to terminate the excitation energy at the first frequency E1 for a first sensing phase during which the sensor assembly 70 senses the first location signal L1 from the first marker 220a without the presence of the excitation energy at the first frequency E1. The controller 80 then causes the excitation source 60 to: (a) generate the second excitation energy at the second frequency E2 for a second excitation period; and (b) terminate the excitation energy at the second frequency E2 for a second sensing phase during which the sensor assembly 70 senses the second location signal L2 from the second marker 220b without the presence of the second excitation energy at the second frequency E2. The controller 80 then repeats this operation with the third excitation energy at the third frequency E3 such that the third marker 220c transmits the third location signal L3 to the sensor assembly 70 during a third sensing phase. As such, the excitation source 60 wirelessly transmits the excitation energy in the form of pulsed magnetic fields at the resonant frequencies of the markers 220a-c during excitation periods, and the markers 220a-c wirelessly transmit the location signals L1-3 to the sensor assembly 70 during sensing phases. It will be appreciated that the excitation and sensing phases can be repeated to permit averaging of the sensed signals to reduce noise.

The computer-operable media in the controller 80, or in a separate signal processor, or other computer also includes instructions to determine the absolute positions of each of the markers 220a-c in a three-dimensional reference frame. Based on signals provided by the sensor assembly 70 that correspond to the magnitude of each of the location signals L1-3, the controller 80 and/or a separate signal processor calculates the absolute coordinates of each of the markers 220a-c in the three-dimensional reference frame. The absolute coordinates of the markers 220a-c are objective data that can be used to calculate the coordinates of the target in the reference frame. When multiple markers are used, the rotation of the target can also be calculated.

2. Real-time Tracking

The localization system 10 and at least one marker 220 enable real-time tracking of the target 2 relative to the machine isocenter or another external reference frame outside of the patient during treatment planning, setup, radiation sessions, and at other times of the radiation therapy process. In many embodiments, real-time tracking means collecting position data of the markers, determining the locations of the markers in an external reference frame, and providing an objective output in the external reference frame that is responsive to the location of the markers. The objective output is provided at a frequency that adequately tracks the target in real time and/or a latency that is at least substantially contemporaneous with collecting the position data (e.g., within a generally concurrent period of time).

For example, several embodiments of real-time tracking are defined as determining the locations of the markers and calculating the location of the target relative to the machine isocenter at (a) a sufficiently high frequency so that pauses in representations of the target location at a user interface do not interrupt the procedure or are readily discernable by a human, and (b) a sufficiently low latency to be at least substantially contemporaneous with the measurement of the location signals from the markers. Alternatively, real time means that the localization system 10 calculates the absolute position of each individual marker 220 and/or the location of the target at a periodicity of 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz).

Alternatively, real-time tracking can further mean that the localization system 10 provides the absolute locations of the markers 220 and/or the target 2 to a memory device, user interface, linear accelerator, or other device within a latency of 10 ms to 5 seconds from the time the localization signals were transmitted from the markers 220. In more specific applications, the localization system generally provides the locations of the markers 220 and/or target 2 within a latency of about 20-50 ms. The localization system 10 accordingly provides real-time tracking to monitor the position of the markers 220 and/or the target 2 with respect to an external reference frame in a manner that is expected to enhance the efficacy of radiation therapy because higher radiation doses can be applied to the target and collateral effects to healthy tissue can be mitigated.

The system described herein uses one or more markers to serve as registration points to characterize target location, rotation, and motion. In accordance with aspects of the invention, the markers have a substantially fixed relationship with the target. If the markers did not have a substantially fixed relationship with the target, another type of tracking error would be incurred. This generally requires the markers to be fixed or positioned sufficiently close to the target in order that tracking errors be within clinically meaningful limits; thus, the markers may be placed in tissue or bone that exhibits representative motion of the target. For example, with respect to the lung, a device that is representative of the target's motion would include a marker retained in bronchi of a patient.

According to aspects of the present invention, the marker motion is a surrogate for the motion of the target. Accordingly, the marker is placed such that it moves in direct correlation to the target being tracked. Depending on the target being tracked, the direct correlation relationship between the target and the marker will vary. For example, with respect to soft tissue that moves substantially in response to the respirations of the patient, such as the lung, the marker may be placed in a bronchi to provide surrogate motion in direct correlation with target motion.

Figure 9:
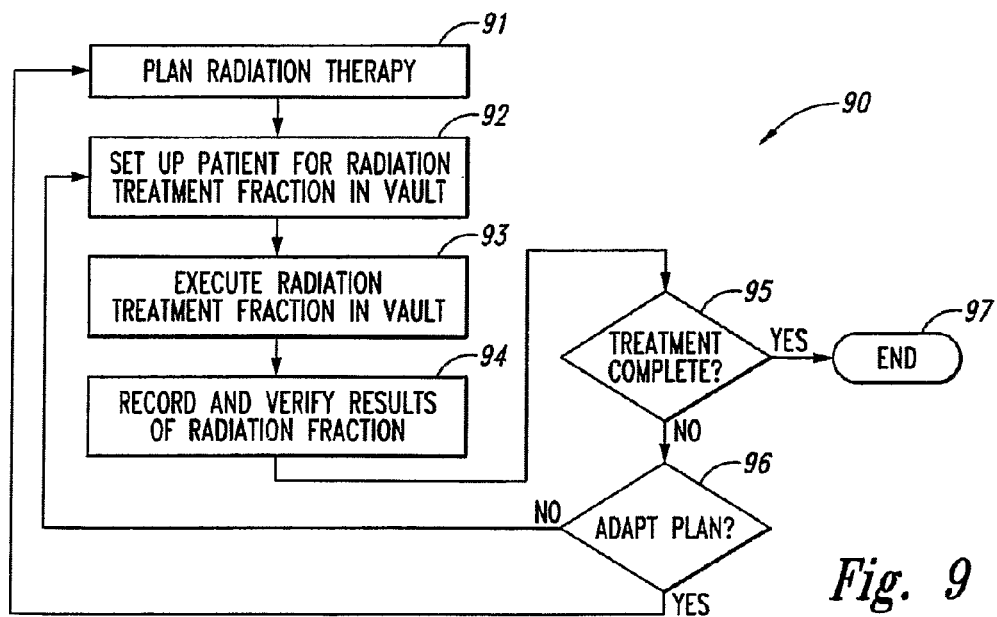
FIG. 9 is a flow diagram illustrating several aspects and uses of real-time tracking to monitor the location and the status of the target in accordance with embodiments of the invention.
Figure 10A:
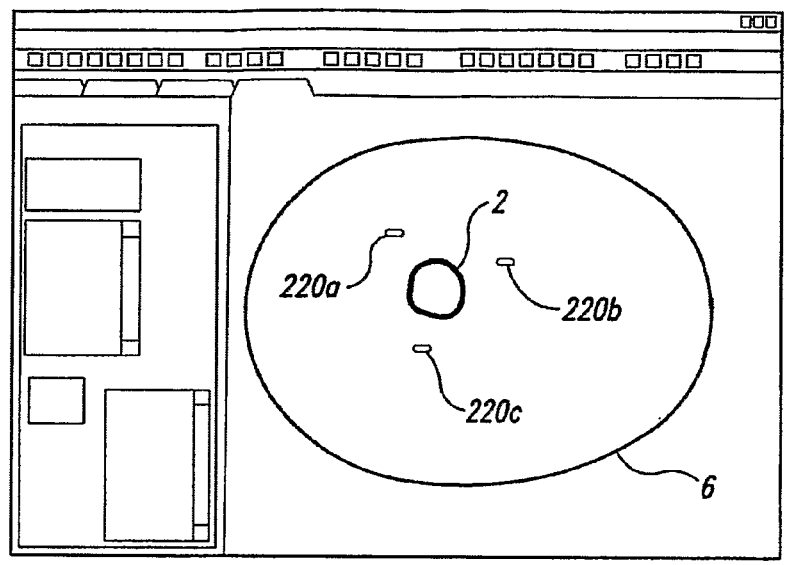
FIGS. 10A and 10B are representations of a CT image showing a cross-section of the patient, the target, and the marker in accordance with embodiments of the invention.
Figure 10B:
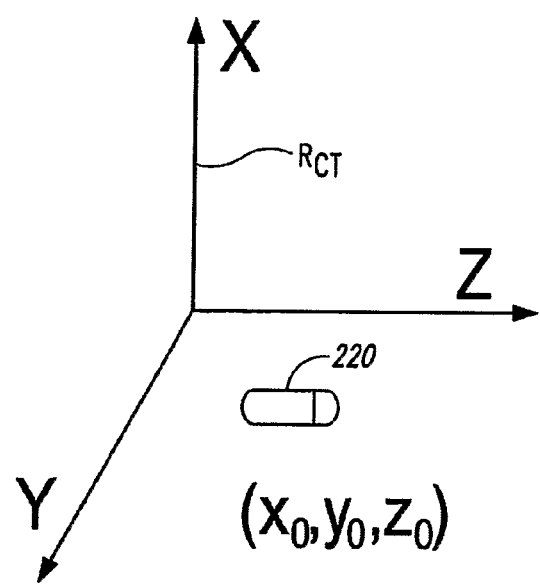

FIG. 9 is a flow diagram illustrating several aspects and uses of real-time tracking to monitor the location and the status of the target. In this embodiment, an integrated method 90 for radiation therapy includes a radiation planning procedure 91 that determines the plan for applying the radiation to the patient over a number of radiation tractions. The radiation planning procedure 91 typically includes an imaging stage in which images of a tumor or other types of targets are obtained using X-rays, CT, MR, or ultrasound imaging. The images are analyzed by a person to measure the relative distances between the markers and the relative position between the target and the markers. FIG. 10A, for example, is a representation of a CT image showing a cross-section of the patient 6, the target 2, and a marker 220. Referring to FIG. 10B, the coordinates (x0, y0, z0) of the marker 220 in a reference frame RCT of the CT scanner can be determined by an operator. The coordinates of the tumor can be determined in a similar manner to ascertain the offset between the marker and the target. Alternatively, the coordinates of a radiographic fiducial 30 in a reference frame RCT of the CT scanner can be determined by an operator.

Figure 11:
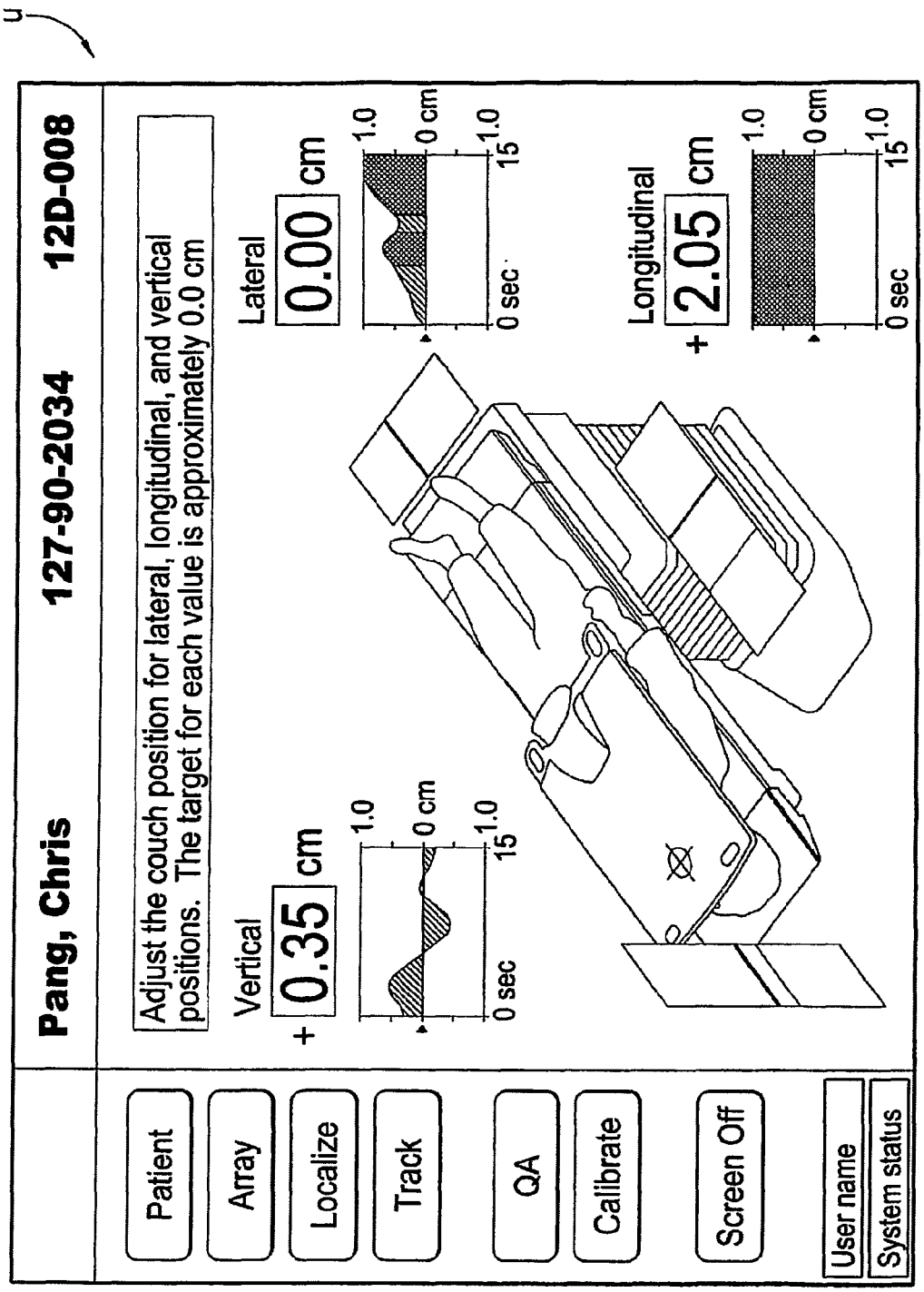
FIG. 11 is a screen shot of a user interface showing the objective offset values can be provided to the user interface showing vertical, lateral, and longitudinal offsets of the target relative to the machine isocenter in accordance with embodiments of the invention.

The localization system 10 and the markers 220 enable an automated patient setup process for delivering the radiation. After developing a treatment plan, the method 90 includes a setup procedure 92 in which the patient is positioned on a movable support table so that the target and markers are generally adjacent to the sensor assembly. As described above, the excitation source is activated to energize the markers, and the sensors measure the strength of the signals from the markers. The computer controller then (a) calculates objective values of the locations of the markers and the target relative to the machine isocenter, and (b) determines an objective offset value between the position of the target and the machine isocenter. Referring to FIG. 11, for example, the objective offset values can be provided to a user interface that displays the vertical, lateral, and longitudinal offsets of the target relative to the machine isocenter. A user interface may, additionally or instead, display target rotation.

One aspect of several embodiments of the localization system 10 is that the objective values are provided to the user interface or other device by processing the position data from the field sensor 70 in the controller 80 or other computer without human interpretation of the data received by the sensor assembly 70. If the offset value is outside of an acceptable range, the computer automatically activates the control system of the support table to move the tabletop relative to the machine isocenter until the target isocenter is coincident with the machine isocenter. The computer controller generally provides the objective output data of the offset to the table control system in real time as defined above. For example, because the output is provided to the radiation delivery device, it can be at a high rate (1-20 ms) and a low latency (10-20 ms). If the output data is provided to a user interface in addition to or in lieu of the table controller, it can be at a relatively lower rate (20-50 ms) and higher latency (50-200 ms).

In one embodiment, the computer controller also determines the position and orientation of the markers relative to the position and orientation of simulated markers. The locations of the simulated markers are selected so that the target will be at the machine isocenter when the real markers are at the selected locations for the simulated markers. If the markers are not properly aligned and oriented with the simulated markers, the support table is adjusted as needed for proper marker alignment. This marker alignment properly positions the target along six dimensions, namely X, Y, Z, pitch, yaw, and roll. Accordingly, the patient is automatically positioned in the correct position and rotation relative to the machine isocenter for precise delivery of radiation therapy to the target.

Figure 12:
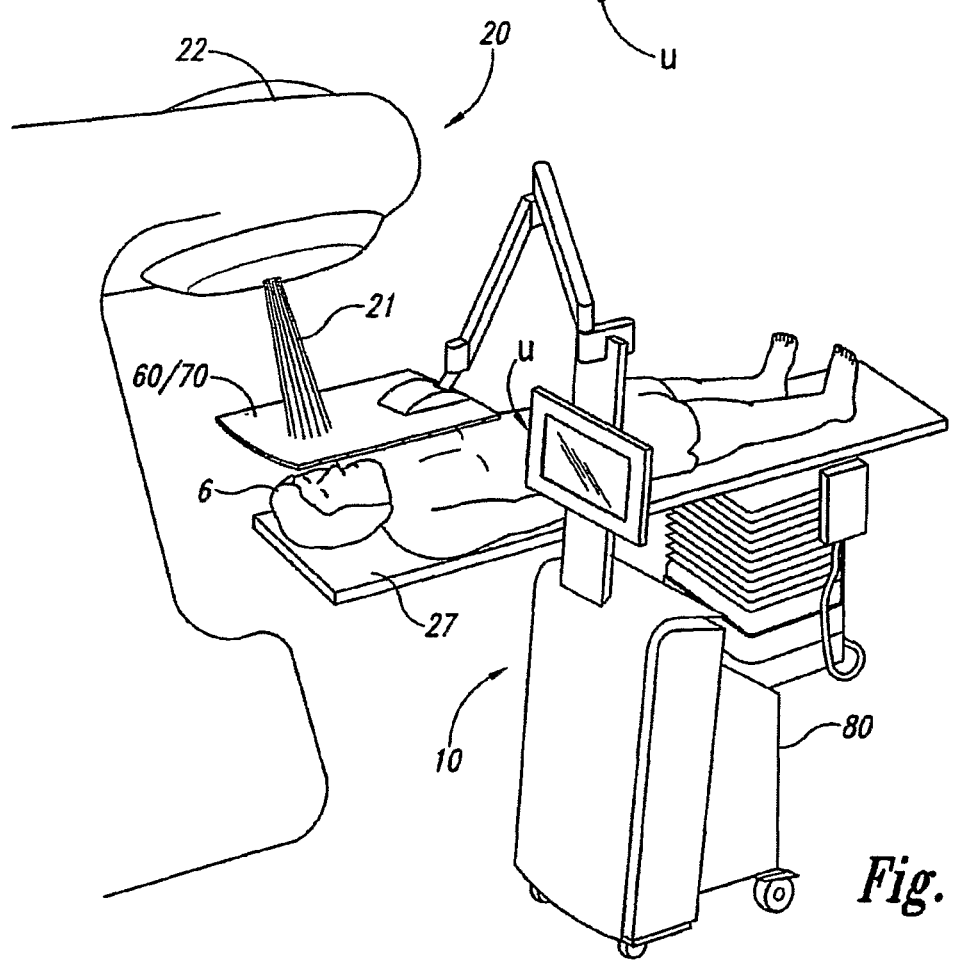
FIG. 12 shows an automated process in which the localization system tracks the target during the radiation session and controls the radiation delivery source according to the offset between the target and the machine isocenter in accordance with embodiments of the invention.

Referring back to FIG. 9, the method 90 further includes a radiation session 93. FIG. 12 shows a further aspect of an automated process in which the localization system 10 tracks the target during the radiation session 93 and controls the radiation delivery source 20 according to the offset between the target and the machine isocenter. For example, if the position of the target is outside of a permitted degree or range of displacement from the machine isocenter, the localization system 10 sends a signal to interrupt the delivery of the radiation or prevent initial activation of the beam. In another embodiment, the localization system 10 sends signals to automatically reposition a table 27 and the patient 6 (as a unit) so that the target isocenter remains within a desired range of the machine isocenter during the radiation session 93 even if the target moves. In still another embodiment, the localization system 10 sends signals to activate the radiation only when the target is within a desired range of the machine isocenter (e.g., gated therapy). In some embodiments, the localization system enables dynamic adjustment of the table 27 and/or the beam 21 in real time while irradiating the patient. Dynamic adjustment of the table 27 ensures that the radiation is accurately delivered to the target without requiring a large margin around the target.

The localization system 10 provides the objective data of the offset and/or rotation to the linear accelerator and/or the patient support table in real time as defined above. For example, as explained above with respect to automatically positioning the patent support table during the setup procedure 92, the localization system generally provides the objective output to the radiation delivery device at least substantially contemporaneously with obtaining the position data of the markers and/or at a sufficient frequency to track the target in real time. The objective output, for example, can be provided at a short periodicity (1-20 ms) and a low latency (10-20 ms) such that signals for controlling the beam 21 can be sent to the radiation delivery source 20 in the same time periods during a radiation session. In another example of real-time tracking, the objective output is provided a plurality of times during an "on-beam" period (e.g., 2, 5, 10, or more times while the beam is on). In the case of terminating or activating the radiation beam, or adjusting the leaves of a beam collimator, it is generally desirable to maximize the refresh rate and minimize the latency. In some embodiments, therefore, the localization system may provide the objective output data of the target location and/or the marker locations at a periodicity of 10 ms or less and a latency of 10 ms or less. The method 90 may further include a verification procedure 94 in which objective output data from the radiation session 93 is compared to the status of the parameters of the radiation beam.

The method 90 can further include a first decision (Block 95) in which the data from the verification procedure 94 is analyzed to determine whether the treatment is complete. If the treatment is not complete, the method 90 further includes a second decision (Block 96) in which the results of the verification procedure are analyzed to determine whether the treatment plan should be revised to compensate for changes in the target. If revisions are necessary, the method can proceed with repeating the planning procedure 91. On the other hand, if the treatment plan is providing adequate results, the method 90 can proceed by repeating the setup procedure 92, radiation session 93, and verification procedure 94 in a subsequent fraction of the radiation therapy.

The localization system 10 provides several features, either individually or in combination with each other, that enhance the ability to accurately deliver high doses of radiation to targets within tight margins. For example, many embodiments of the localization system use leadless markers that are substantially fixed with respect to the target. The markers accordingly move either directly with the target or in a relationship proportional to the movement of the target. Moreover, many aspects of the localization system 10 use a non-ionizing energy to track the leadless markers in an external, absolute reference frame in a manner that provides objective output. In general, the objective output is determined in a computer system without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

G. Embodiments of Anchorable Markers

Figure 13G:
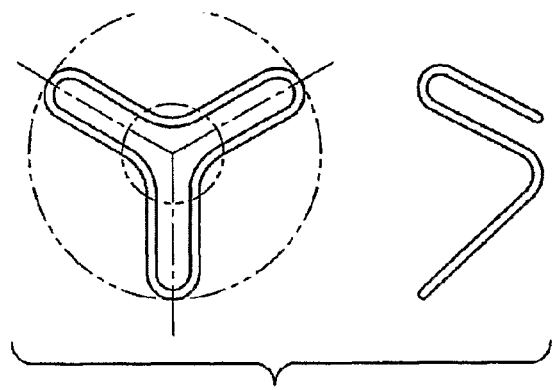
FIGS. 13A-13X are isometric, cross-sectional and end views of markers in accordance with embodiments of the invention.
Figure 13H:
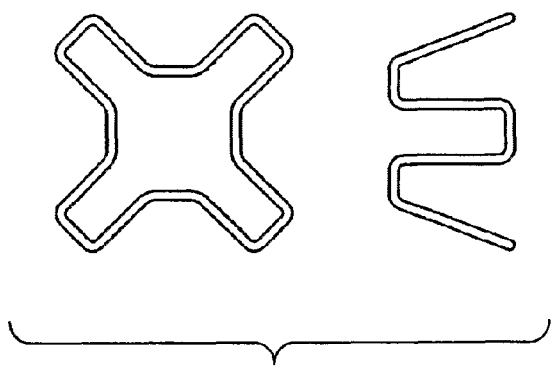
Figure 13I:
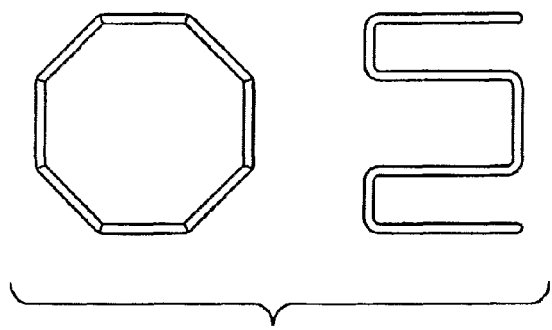
Figure 13J:
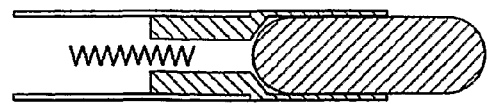
Figure 13K:
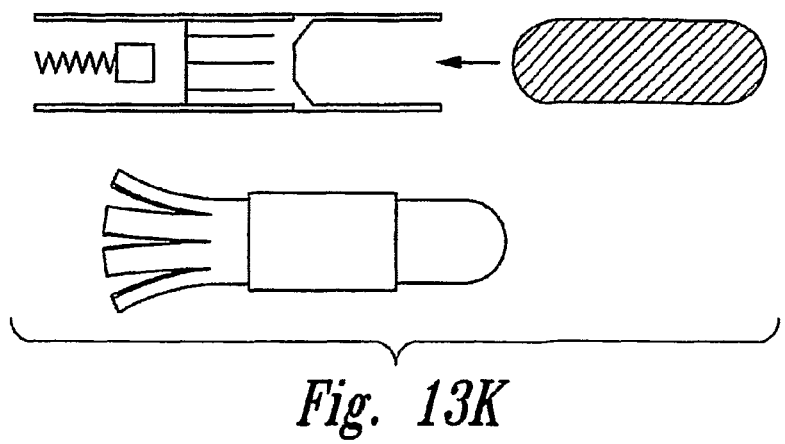
Figure 13L:
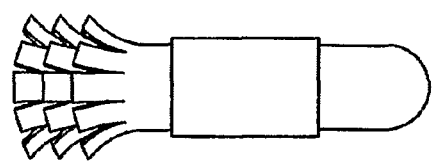
Figure 13M:
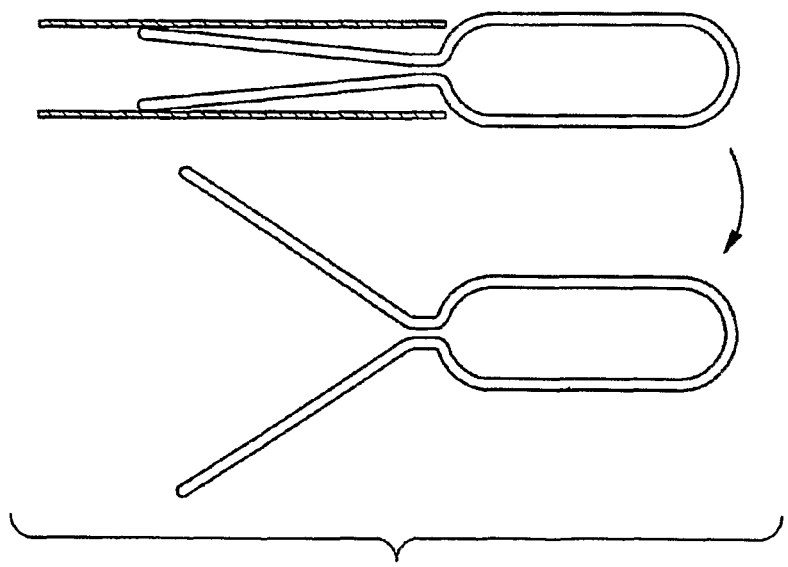
Figure 13N:
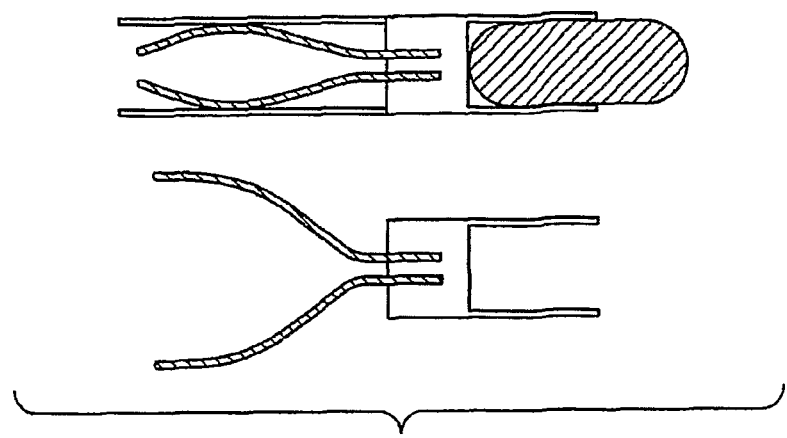
Figure 13O:
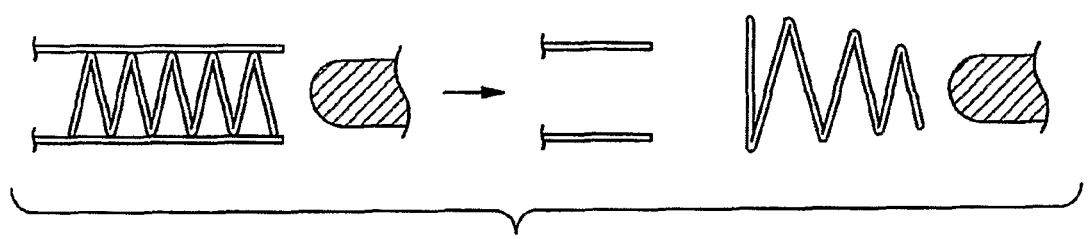
Figure 13P:
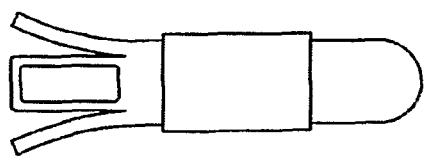
Figure 13Q:
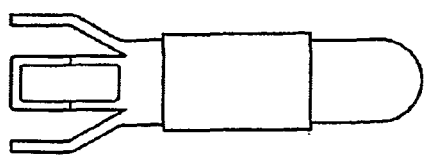

FIGS. 13A-13X are side elevation, cross-sectional and end views of markers in accordance with different embodiments of the invention. Referring to FIG. 13A, a marker includes a casing 802, a magnetic transponder (e.g., a resonating circuit) at least partially encased in the casing, and an anchor 810. The casing is a biocompatible barrier, which can be made from plastics, ceramics, glass or other suitable materials, and the casing is configured to be implanted in the patient. The casing can be a generally cylindrical capsule that is sized to fit within a catheter for bronchoscopic implantation. For example, the casing can have a diameter of approximately 2 mm or less. According to aspects of the invention, the casing can have a slightly larger diameter than the inside diameter of the delivery catheter 212 to retain the casing in the catheter during placement.

Generally, the magnetic transponder can include a resonating circuit that produces a wirelessly transmitted signal in response to a wirelessly transmitted excitation field. In one embodiment, the magnetic transponder comprises a coil defined by a plurality of windings around a conductor. Many embodiments of the magnetic transponder also include a capacitor coupled to the coil. The coil can resonate at a resonant frequency solely using the parasitic capacitance of the windings without having a capacitor, or the resonant frequency can be produced using the combination of the coil and the capacitor. The coil accordingly defines a signal transmitter that generates an alternating magnetic field at the selected resonant frequency in response to the excitation energy either by itself or in combination with the capacitor. The coil generally has 800-2000 turns, and the windings are preferably wound in a tightly layered coil.

The magnetic transponder can further include a core composed of a material having a suitable magnetic permeability. For example, the core can be a ferromagnetic element composed of ferrite or another material. Suitable embodiments of magnetic transponders are disclosed in U.S. patent application Ser. Nos. 10/334,698 and 10/746,888, which are incorporated herein by reference in their entirety.

FIGS. 13A-13X are side elevational vies, cross-sectional views, and end views of several implantable markers in accordance with embodiments of the invention. The implantable markers shown in FIGS. 13A-13X illustrate a variety of fasteners 810 in accordance with embodiments of the invention. The implantable marker shown in FIG. 13A includes a fastener 810 defined by legs that project away from the casing in the deployed position. The legs can be molded projections of the casing, or the legs can be small springs biased to project away from the casing once deployed from the delivery channel. The implantable marker shown in FIG. 13B includes a fastener 810 defined by shape-memory loops on both ends of the casing. In FIG. 13C, the implantable marker has a fastener 810 defined by surface texture, such as scales that project away from the casing. The surface texture of the implantable marker can be integrally formed with the casing. Referring to FIG. 13D, the implantable marker can include a fastener 810 defined by one or more barbs or hooks. Referring to FIG. 13E, the implantable marker includes a fastener 810 defined by a spring or serpentine element extruding from the rear of the casing. FIGS. 13F-13X include further configurations of implanted markers. It will be appreciated that the fasteners 810 can have different configurations than the particular types of fasteners 810 shown in FIGS. 13A-13X.

Several of the embodiments shown in FIGS. 13A-13X illustrate fastener 810 or anchor protruding from the marker casing wherein the fastener 810 can be an integral extension of the casing. Alternatively, the fastener 810 can be a separate component attached to and/or embedded in the casing. According to aspects of the invention, the anchor may be embedded in the marker or the anchor may be contained in the delivery catheter such that the anchor is deployed adjacent to the marker to prevent the marker from migrating. When the fastener 810 is a separate component, it can be made from a suitable biocompatible material, such as metals, metal alloys, or polymers and other synthetic materials. An example of one such material is spring steel, although other "memory" metal alloys such as Nitinol® may be suitable. According to further aspects of the invention, an outer shape can employ shape memory alloy features that "grow" into bronchiole as internal body temp expands the alloy.

Another embodiment of a marker comprises a marker section configured to be localized and an anchor attached to the marker section. The anchor comprises an expandable member that moves between a stored position having a first size and a deployed position having a second size greater than the first size. The anchor, for example, can be a stent, an umbrella-like expandable member, or an expandable cylindrical section as shown in FIGS. 13F, 13K, 13L, 13M, 13N, 13L, 13O, 13P, 13Q, and 13R.

Alternative anti-migration devices and methods that prevent the transponder from moving from the implantation position to a more proximal position relative to the trachea include positioning the anti-migration device either behind the transponder in the catheter or delivered through the catheter after transponder deployment (e.g., glue). Additionally, glue or other chemical material may be delivered through the delivery catheter to function as an anti-migration device. The glue may be pre-packaged within the catheter or injected through the catheter after implantation. Alternatively, a hydroscopic material that expands due to contact with bodily fluids may act as an anti-migration device, for example, a hydrogel, a hygroscopic material, and/or a sponge. According to yet another embodiment, suture material may be pushed out of the catheter and compacted to plug the vessel and serve as an anti-migration device.

FIG. 14A is a cross-sectional view illustrating an embodiment of one of the markers 1440. In this embodiment, the marker 1440 includes a transponder 1442 including a core 1444, a coil 1446 around the core 1444, and a capacitor 1448 electrically coupled to the coil 1446. The core 1444 is typically composed of ferrite, and the coil 1446 includes a plurality of windings of a wire around the core 1444. The transponder 1442 can be contained in a capsule 49 configured to be implanted into the patient. The capsule 1449 is typically a biocompatible material. The transponder 1442 has a small cross-sectional dimension in many applications. For example, the transponder 1442 can have a cylindrical portion with a diameter from 0.5-3 mm and desirably from 1-2 mm. The transponder 1442 is a resonating magnetic circuit that receives a wirelessly transmitted excitation energy and produces a wirelessly transmitted location signal in response to the excitation energy. The transponder 1442 accordingly has a resonant frequency at which the excitation energy powers a transponder. Several specific details of different embodiments of localization systems and markers are described further herein.

The marker 1440 shown in FIG. 14A also includes an anchor for attaching the marker 1440 to a passageway in or adjacent to the lung 4 of the patient 6. The anchor 1450 shown in FIG. 14A is a helical stent attached to the capsule 1449. The anchor 1450 moves radially with respect to the longitudinal axis of the marker between a retracted position and a deployed position. The anchor 1450, for example, can have a first diameter D1 in the retracted position to fit within a bronchoscope or a percutaneous trans-thoracic introducer. After being ejected from the introducer, the anchor 1450 expands to a second diameter D2 larger than the first diameter D1 in the deployed position to engage the inner wall of a lumen (e.g., respiratory passageway). In operation, the anchor 1450 presses radially outward against the inner wall of the lumen to hold the marker 1440 in the passageway. The anchor 1450 can also have other embodiments as set forth in the U.S. application Ser. No. 10/438,550, which is incorporated herein by reference, and the anchor 1450 can be used with any of the markers described herein.

Figure 14B:
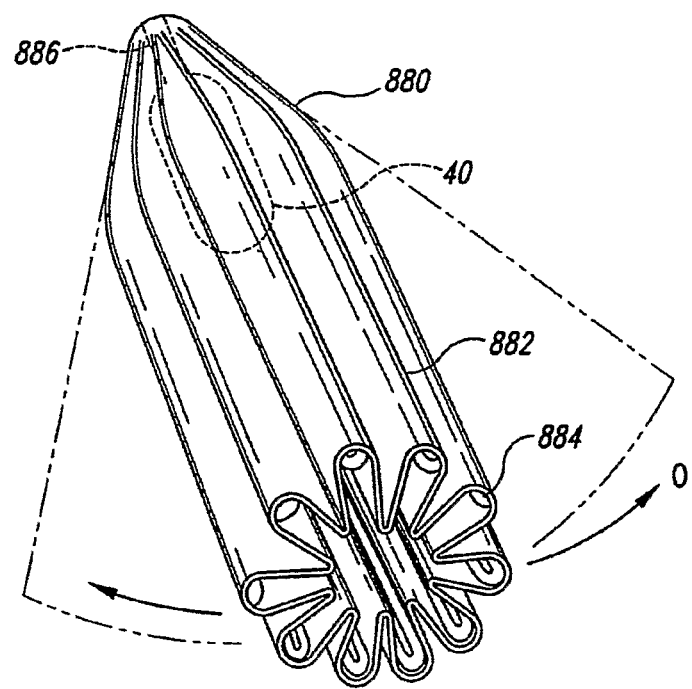
FIG. 14B is an isometric view of a marker and an anchor in accordance with another embodiment of the invention.

FIG. 14B illustrates the marker 40 with another embodiment of an anchor 880 for securing the marker 40 within a passageway in or near the lung 4 of the patient 6. The anchor 880 includes an umbrella-like cover 882 supported by a plurality of links 884 that move outwardly (arrow 0) from a stored position shown in solid lines to a deployed position shown in broken lines. The marker 880 further includes a tether or attachment device 886 connecting the marker 40 to the anchor 880. In operation, the anchor 880 expands into the deployed position to hold the marker within the lumen as the marker is released from a catheter or bronchoscope.

Figure 14C:
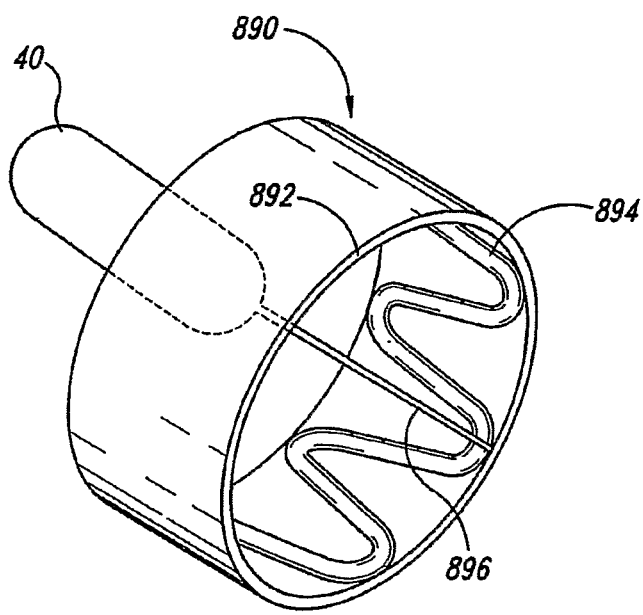
FIG. 14C is an isometric view of a marker and an anchor in accordance with another embodiment of the invention.

FIG. 14C illustrates the marker 40 with an anchor 890 in accordance with another embodiment of the invention. In this embodiment, the anchor 890 includes a cylindrical section 892 and a resilient member 894 attached to the cylindrical section 892 for urging the cylindrical 892 radially outward. The anchor 890 further includes a tether 896 attaching the marker 40 the anchor 890. The anchors 880 and 890 and other suitable anchors for deployment of the markers 40 are disclosed in the following U.S. patents and U.S. patent application publication, which are herein incorporated by reference in their entirety: U.S. Pat. Nos. 6,258,100 B1; 6,592,594 B2; and 2003/0212412 A1.

The markers are well suited for bronchoscopic implantation because they can fit within the delivery channel in the undeployed state and automatically expand upon being ejected or deployed from the delivery channel. According to aspects of the present invention, the marker may block the bronchial vessel and prevent ventilation to more distal lung tissue. According to one embodiment, the marker may be implanted within vessels that provide ventilation for a small volume of the overall lung capacity. The volume of lung capacity affected should be less than 5% and preferably less than 2%. One or more transponders may be implanted to localize one or more therapy targets. For example, occluding a bronchial vessel of 2.5 mm in diameter with a transponder would affect ventilation to approximately 0.5% of the overall lung volume for a patient with healthy lungs.

H. Method of Implanting a Marker Bronchoscopically

Method of implanting a marker bronchoscopically includes pre-loading delivery catheter with a marker such that the marker is flush with a distal end of the delivery catheter or extending a selected distance beyond the distal end of the delivery catheter, passing the delivery catheter through the working channel of a bronchoscope, advancing the catheter into desired position adjacent to tumor or lesion in lung, deploying the marker, and withdrawing delivery catheter. The catheter can be pre-loaded during manufacturing and sterilization or preloaded in the operating room just prior to implantation. Deploying the marker can include axially moving a push wire to engage the marker at a distal end to deploy the marker at the desired anatomical location. Alternatively, fluid may be used in the working channel in place of a push wire. In yet another embodiment, fluid and a push wire may be used in combination to deploy the marker.

According to aspects of the invention, the delivery catheter can be pre-loaded with multiple markers to allow multiple deployments in one location. In this embodiment, the push wire between the actuator and the housing may further include markers to delineate the appropriate distance to push the push wire in order to deploy one marker, a second appropriate distance to deploy a second distance and as for as many markers as need to be deployed. In operation, the delivery catheter can be pre-loaded with multiple markers and the catheter can be moved between marker deployments to deploy a first marker in a first location, move the catheter, deploy a second marker in a second location and so on. The bronchoscope can be placed in a first location such that a distal end is adjacent to a tumor a lesion; the delivery catheter can be pre-loaded with multiple markers; the delivery catheter can be inserted into a working channel of the bronchoscope; the actuator can be moved to deploy a first marker; the delivery catheter and/or the bronchoscope can be repositioned to a second location such that the distal end is adjacent to the tumor or lesion; the actuator can be moved to deploy a second marker, and so on until all of the markers are deployed.

I. Method of Reducing Pneumothorax When Implanting a Marker Bronchoscopically

A method of reducing pneumothorax when implanting a marker bronchoscopically includes pre-loading the delivery catheter with a marker configured with a rounded leading edge extending a selected distance beyond a distal end of the delivery catheter, passing the delivery catheter through the working channel of a bronchoscope, advancing the delivery catheter into the desired position adjacent to tumor or lesion in lung, deploying the marker in the desired position, withdrawing catheter. Deploying the marker can include axially moving a push wire to engage the marker at a distal end to deploy the marker is the desired anatomical location. According to aspects of the invention, the delivery catheter can be pre-loaded with multiple markers to allow multiple deployments in one location. Alternatively, the delivery catheter can be pre-loaded with multiple markers and moved between marker deployments to deploy a first marker in a first location, moving the delivery catheter, deploying a second marker in a second location and so on.

J. Conclusion

From the foregoing, it will be appreciated that specific embodiments of the invention have been described herein for purposes of illustration, but that various modifications may be made without deviating from the spirit and scope of the invention. Accordingly, the invention is not limited except as by the appended claims. The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to wireless markers, including gold seeds, not necessarily the exemplary electromagnetic transponders generally described above.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless the context requires otherwise, throughout the specification and claims which follow, the word "comprise" and variations thereof, such as, "comprises" and "comprising" are to be construed in an open, inclusive sense, which is as "including, but not limited to."

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the invention can be modified, if necessary, to employ systems, catheters, markers and concepts of the various patents, applications and publications to provide yet further embodiments of he invention.

These and other changes can be made to the invention in light of the above-detailed description. In general, in the following claims, the terms used should not be construed to limit the invention to the specific embodiments disclosed in the specification and the claims, but should be construed to include all markers that operated in accordance with the claims. Accordingly, the invention is not limited by the disclosure, but instead its scope is to be determined entirely by the following claims.

We claim:

1. A catheter assembly for delivering a marker into a lumen, the assembly comprising:
   a catheter having a proximal end and a distal end, the distal end configured to receive a marker, the distal end of the catheter configured to provide a rounded leading edge, wherein
      the catheter is configured to be passed into a lumen for deployment of the marker, and
      the distal end of the catheter has an unexpanded state and an expanded state;
   at least one marker contained at the distal end of the catheter, wherein the marker comprises a signal element configured to transmit location signals in response to an excitation energy, wherein
      when the distal end of the catheter is in the unexpanded state before the marker is loaded in the catheter, the marker has an outer diameter greater than an inner diameter of the distal end of the catheter, and
      when the distal end of the catheter is in the expanded state, the distal end of the catheter releasably retains the marker by expanding around the marker;
   an actuator having a housing coupled to a proximal end of the catheter and moveable between a first position and a second position; and
   a wire fixedly attached to the actuator, wherein the wire is contained in the catheter and extends co-axially substantially the entire length of the catheter.

2. The assembly of claim 1, further configured such that the distal end of the catheter has no sharp edges that could puncture the luminal wall during implantation.

3. The assembly of claim 1 wherein the marker is shaped and positioned in the catheter such that no sharp edges are present that could puncture the luminal wall during implantation.

4. The assembly of claim 3, further comprising a supply and loading device matably coupled with the distal end of the catheter and configured to releasably retain at least one stored marker and transfer the marker from the supply and loading device to the distal end of the catheter.

5. The assembly of claim 4, wherein the supply and loading device includes a storage portion configured to releasably store the marker in a stored position and an interface port configured to receive a distal end of the catheter to provide transfer of the marker from the supply and loading device to the catheter.

6. The assembly of claim 3, further comprising an anti-migration device contained at the distal end of the catheter, wherein the anti-migration device prevents movement of the marker within the lumen.

7. The assembly of claim 3, wherein the catheter and wire have dimensions such that the assembly can be passed down a working channel of a bronchoscope a selected distance for deployment of the marker in a bronchial lumen within the lung.

8. A bronchoscopic catheter assembly for delivering a marker into a passageway, the assembly comprising:
   at least one marker including a magnetic transponder;
   a catheter having a proximal end and a distal end, the catheter configured to be passed down a working channel of a bronchoscope a selected distance to a location in a passageway for deployment of the marker, wherein
      the distal end of the catheter is made of a flexible material and has an inner diameter before the marker is received in the distal end,
      the marker has an outer diameter greater than the inner diameter of the distal end of the catheter,
      the distal end of the catheter is configured to expand around the marker to releasably retain the marker prior to deployment, and
      when the marker is pre-loaded in the distal end of the catheter, a portion of the marker extends beyond the distal end of the catheter and is configured to provide a rounded leading edge;
   an actuator having a housing coupled to a proximal end of the catheter and moveable between a first position and a second position; and
   a push wire fixedly attached to the actuator, wherein the push wire is contained in the catheter and extends co-axially substantially the entire length of the catheter.

9. The assembly of claim 8 wherein the marker is configured to minimize sharp edges that could punch the visceral pleura during implantation.

10. The assembly of claim 9, further comprising an anti-migration device contained at the distal end of the catheter, wherein the anti-migration device prevents migration of the marker.

* * * * *